United States Patent
Mansour et al.

(10) Patent No.: US 11,667,612 B2
(45) Date of Patent: Jun. 6, 2023

(54) COMPOSITIONS AND METHODS FOR DELIVERING PHARMACEUTICAL AGENTS

(71) Applicant: Arizona Board of Regents on Behalf of the University of Arizona, Tucson, AZ (US)

(72) Inventors: Heidi M. Mansour, Tucson, AZ (US); Jason Yuan, Tucson, AZ (US); Jian Wang, Tucson, AZ (US); Alexan I. Gomez, Tucson, AZ (US); Priyardarshini Muralidharan, Tucson, AZ (US); Yali Gu, Tucson, AZ (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 267 days.

(21) Appl. No.: 16/759,100

(22) PCT Filed: Oct. 25, 2018

(86) PCT No.: PCT/US2018/057549
§ 371 (c)(1),
(2) Date: Apr. 24, 2020

(87) PCT Pub. No.: WO2019/084292
PCT Pub. Date: May 2, 2019

(65) Prior Publication Data
US 2021/0179566 A1    Jun. 17, 2021

Related U.S. Application Data

(60) Provisional application No. 62/576,956, filed on Oct. 25, 2017.

(51) Int. Cl.
| | |
|---|---|
| *C07D 241/12* | (2006.01) |
| *A61K 9/00* | (2006.01) |
| *A61K 31/4965* | (2006.01) |
| *A61K 45/06* | (2006.01) |
| *A61K 47/26* | (2006.01) |

(52) U.S. Cl.
CPC .......... *C07D 241/12* (2013.01); *A61K 9/0075* (2013.01); *A61K 31/4965* (2013.01); *A61K 45/06* (2013.01); *A61K 47/26* (2013.01); *C07B 2200/13* (2013.01)

(58) Field of Classification Search
CPC .. C07D 241/00; C07D 241/02; A61K 31/495; A61K 31/4965; A61P 9/00
See application file for complete search history.

(56) References Cited

U.S. PATENT DOCUMENTS

| | | | |
|---|---|---|---|
| 6,225,471 B1 * | 5/2001 | Chen | C07D 241/12 544/410 |
| 6,766,799 B2 | 7/2004 | Edwards et al. | |
| 6,848,197 B2 | 2/2005 | Chen et al. | |
| 7,278,425 B2 | 10/2007 | Edwards et al. | |
| 8,197,845 B2 | 6/2012 | Hartig et al. | |
| 8,496,002 B2 | 7/2013 | Ellwanger et al. | |
| 2003/0125233 A1 * | 7/2003 | Carmeliet | A61K 38/57 514/1 |
| 2011/0200531 A1 | 8/2011 | Tan | |
| 2012/0115874 A1 | 5/2012 | Wang et al. | |
| 2019/0177258 A1 * | 6/2019 | Emanuele | A61K 9/14 |

FOREIGN PATENT DOCUMENTS

| | | | |
|---|---|---|---|
| CN | 101152182 A | * | 4/2008 |
| CN | 101919855 A | * | 12/2010 |
| CN | 102060787 A | * | 5/2011 |
| CN | 101647781 | | 6/2011 |
| CN | 105213328 A | * | 1/2016 |

OTHER PUBLICATIONS

Acosta, MF, et al., n Vitro Pulmonary Cell Culture in Pharmaceutical Inhalation Aerosol Delivery: 2-D, 3-D, and In Situ Bioimpactor Models. Current pharmaceutical design. 2016;22(17):2522-2531.
Cai, Y, et al., Proceedings of the Chinese Academy of Medical Sciences and the Peking Union Medical College 1988;4(3):147-152.
Chang, et al., Effects of Tetramethylpyrazine on Portal Hypertensive Rats. Journal of pharmacy and pharmacology. 1998;50(8):881-884.
Farber, HW, et al., Pulmonary Arterial Hypertension. New England Journal of Medicine. 2004;351(16):1655-1665.
Gessler, T, et al., Inhaled Prostanoids in the Therapy ofPulmonary Hypertension. Journal of aerosol medicine and pulmonary drug delivery. 2008;21(1):1-12.
Heyder, J. Deposition of Inhaled Particles in the Human Respiratory Tract and Consequences for Regional Targeting in Respiratory Drug Delivery. Proceedings of the American Thoracic Society. 2004;1(4):315-320.
Hickey, AJ, et al., Formulation Callenges of Powders for the Delivery of Small Molecular-Weight Molecules as Aerosols. Drugs and the Pharmaceutical Sciences. 2003;126:835-848.
Hill, NS, et al., Inhaled Therapies for Pulmonary Hypertension. Respiratory care. 2015;60(6):794-805.
Jain, et al., Spray Drying in Pharmaceutical Industry: A Review. Research J. Pharma. Dosage Forms and Tech. 2011; 4(2): 74-79.
Kuhr, FK, et al., New mechanisms of pulmonary arterial hypertension: role of Ca2+ signaling. American Journal of Physiology-Heart and Circulatory Physiology. 2012;302(8):H1546-H1562.
Li, SY, et al., Stabilization of mitochondrial function by tetramethylpyrazine protects against kainate-induced oxidative lesions in the rat hippocampus. Free radical biology & medicine. Feb. 15, 2010;48(4):597-608.

(Continued)

*Primary Examiner* — Theodore R. Howell
*Assistant Examiner* — George W Kosturko
(74) *Attorney, Agent, or Firm* — Casimir Jones, S.C.; Tanya A. Arenson

(57) ABSTRACT

Provided herein are compositions and methods for treating pulmonary arterial hypertension. In particular, provided herein are dry powder formulations of TMP for delivery to the lung.

12 Claims, 24 Drawing Sheets

(56) References Cited

OTHER PUBLICATIONS

Li, X, et al., Physicochemical characterization and aerosol dispersion performance of organic solution advanced spray-dried microparticulate/nanoparticulate antibiotic dry powders of tobramycin and azithromycin for pulmonary inhalation aerosol delivery. European Journal of Pharmaceutical Sciences. 2014;52:191-205.

Li, X, et al., Physicochemical Characterization and Water Vapor Sorption of Organic Solution Advanced Spray-Dried Inhalable Trehalose Microparticles and Nanoparticles for Targeted Dry Powder Pulmonary Inhalation Delivery. Journal of aerosol medicine and pulmonary drug delivery. 2014;27(2):81-93.

Li, X., et al., Design, characterization, and aerosol dispersion performance modeling of advanced co-spray dried antibiotics with mannitol as respirable microparticles/nanoparticles for targeted pulmonary delivery as dry powder inhalers. Journal of pharmaceutical sciences. 2014;103(9):2937-2949.

Li, X, Mansour HM., Physicochemical Characterization and Water Vapor Sorption of Organic Solution Advanced Spray-Dried Inhalable Trehalose Microparticles and Nanoparticles for Targeted Dry Powder Pulmonary Inhalation Delivery. AAPS PharmSciTech. Dec. 2011;12(4):1420-1430.

Liu, S et al., Ligustrazine is a vasodilator of human pulmonary and bronchial arteries. European journal of pharmacology. 1990; 191(3):345-350.

Mansour, HM, et al., Nanomedicine in pulmonary delivery. Int J Nanomedicine. 2009;4:299-319.

Mansour, HM, et al., Lipid Nanoparticulate Drug Delivery and Nanomedicine. Lipids in Nanotechnology: American Oil Chemists Society Press, Chicago, III; 2011:221-268.

Marple, VA, et al., Next Generation Pharmaceutical Impactor (A New Impactor for Pharmaceutical Inhaler Testing). Part I: Design. Journal of aerosol medicine. 2003;16(3):283-299.

Meenach, SA, et al., High-Performing Dry Powder Inhalers of Paclitaxel DPPC/DPPG Lung Surfactant-Mimic Multifunctional Particles in Lung Cancer: Physicochemical Characterization, In Vitro Aerosol Dispersion, and Cellular Studies. AAPS PharmSciTech. 2014; 15(6):1574-1587.

Meenach, SA, et al., Development of three-dimensional lung multicellular spheroids in air- and liquid-interface culture for the evaluation of anticancer therapeutics. Apr. 2016;48(4):1701-1709.

Meenach, SA, et al., Characterization and aerosol dispersion performance of advanced spray-dried chemotherapeutic PEGylated phospholipid particles for dry powder inhalation delivery in lung cancer. European Journal of Pharmaceutical Sciences. 2013;49(4):699-711.

Meenach, SA, et al., Inhalable nanoparticulate powders for respiratory delivery. Int J Nanomedicine. 2013;8:275-293.

Muralidharan P, et al., Microparticulate/nanoparticulate powders of a novel Nrf2 activator and an aerosol performance enhancer for pulmonary delivery targeting the lung Nrf2/Keap-1 pathway, Molecular Systems Design & Engineering. 2016, 1, 48-65.

Muralidharan, P, et al., Inhalable nanoparticulate powders for respiratory delivery. Nanomedicine: Nanotechnology, Biology and Medicine. 2015; 11(5):1189-1199.

Muralidharan, P, et al., Inhalable PEGylated Phospholipid Nanocarriers and PEGylated Therapeutics for Respiratory Delivery as Aerosolized Colloidal Dispersions and Dry Powder Inhalers. Pharmaceutics. 2014;6(2):333-353.

Oddoy, A, et al., Effects of ligustrazine on the pressure/flow relationship In Is.olated perfused rat lungs. European Respiratory Journal. 1991;4(10):1223-1227.

Olschewski, H, et al., Inhaled Iloprost for Severe Pulmonary Hypertension. The New England journal of medicine. Aug. 1, 2002;347(5):322-329.

Patton, JS, Byron PR. Inhaling medicines: delivering drugs to the body through the lungs. Nature Reviews Drug Discovery. 2007;6(1):67-74.

Simonneau, G, et al., Updated clinical classification of pulmonary hypertension. J. Am. Coll Cardiol, 2013; 62(25 Suppl):D34-D41.

Stenmark, K, et al., Cellular and Molecular Mechanisms of Pulmonary Vascular Remodeling. Annual Review of Physiology. 1997;59(1):89-144.

Stocke, NA, et al., Formulation and Characterization of Inhalable Magnetic Nanocomposite Microparticles (MnMs) for Targeted Pulmonary Delivery via Spray Drying. International journal of pharmaceutics. 2015;479(2):320-328.

Tan, F, et al., Ligustrazine reduces blood-brain barrier permeability in a rat model of focal cerebral ischemia and reperfusion. Experimental and therapeutic medicine. May 2015;9(5):1757-1762.

Thakkar, S, et al., Amorphous or Crystalline? A Comparison of Particle Engineering Methods and Selection. Current pharmaceutical design. 2015;21(40):5789-5801.

Tissot, C, et al., Review of inhaled iloprost for the control of pulmonary artery hypertension in children. Vascular health and risk management. 2009;5(1):325-331.

Wang, Y, et al., Ligustrazine improves blood circulation by suppressing Plateletactivation in a rat model of allergic asthma. Environmental toxicology and pharmacology. Jul. 2016;45:334-339.

Wu, X, et al., Design and physicochemical characterization of advanced spray-dried tacrolimus multifunctional particles for inhalation. Drug design, development and therapy. 2013;7:59-72.

Wu, X, et al., Physicochemical characterization and aerosol dispersion performance of organic solution advanced spray-dried cyclosporine A multifunctional particles for dry powder inhalation aerosol delivery. Int J Nanomedicine. 2013;8:1269-1283.

Xu, Z, et al., Particle Interactions in Dry Powder Inhaler Unit Processes: A Review. Journal of Adhesion Science and Technology. 2011;25(4-5):451-482.

International Search Report and Written Opinion, International Patent Application No. PCT/US2018/057549, dated Jan. 7, 2019, 8 pages.

* cited by examiner

Raw TMP

SD TMP

A

B

COMPOSITIONS AND METHODS FOR DELIVERING PHARMACEUTICAL AGENTS

CROSS REFERENCE TO RELATED APPLICATION

This application is a U.S. 371 national phase entry of International Patent Application No. PCT/US2018/057549, filed Oct. 25, 2018, which claims priority to and the benefit of U.S. Provisional Application No. 62/576,956, filed Oct. 25, 2017, which are hereby incorporated by reference in their entireties.

FIELD

Provided herein are compositions and methods for treating pulmonary arterial hypertension. In particular, provided herein are dry powder formulations of TMP for delivery to the lung.

BACKGROUND

Pulmonary hypertension (PH) is clinically classified into 5 categories (Simonneau G, et al., J. Am. Coll Cardiol, 2013; 62(25 Suppl):D34-D41): 1) Pulmonary arterial hypertension (PAH), 2) Pulmonary hypertension due to left sided heart disease, 3) Pulmonary hypertension related to lung disease or hypoxia, 4) Chronic thromboembolic pulmonary hypertension, 5) Pulmonary hypertension related to multifactorial mechanisms. Pulmonary arterial hypertension (PAH) is one of the most devastating chronic diseases of the pulmonary circulation. In addition to patients with idiopathic and heritable PAH, PAH can also be found in patients in the setting of collagen vascular disease (e.g., localized cutaneous systemic sclerosis), portal hypertension, congenital left-to-right intracardiac shunts, infections with the human immunodeficiency virus (HIV), and persistent pulmonary hypertension of the newborn (Farber H W, et al., New England Journal of Medicine. 2004; 351(16):1655-1665). Pulmonary hypertension (PH) associated with lung diseases and hypoxia can be encountered by healthy individuals living in high altitude, divers, mountain climber, athletes, and during exercise and rehabilitation (Stenmark K, et al., Annual Review of Physiology. 1997; 59(1):89-144). PH is defined clinically as a mean pulmonary arterial pressure of ≥25 mmHg at rest or ≥30 mmHg during exercise (Hill N S, et al., Respiratory care. 2015; 60(6):794-805; Kuhr F K, et al., American Journal of Physiology-Heart and Circulatory Physiology. 2012; 302(8):H1546-H1562). In patients with PAH and PH associated lung diseases and hypoxia, the increased PAP can be attributed to combined effects of sustained vasoconstriction, concentric vascular remodeling, in situ thrombosis, and arterial wall stiffening, resulting in elevated pulmonary vascular resistance (Kuhr et al., supra). As a consequence, elevated pulmonary vascular resistance increases the right heart afterload and in the fullness of time results in right ventricular hypertrophy and eventually right heart failure and death (Kuhr et al., supra).

Currently, there is no cure for PAH; however, treatments have improved dramatically offering both reliefs from symptoms and prolonged survival. The current therapies fall into several classes, including vasodilators, anticoagulants, antiproliferative agents, anti-inflammatory agents, and vascular-remodeling regression therapies (Farber et al., supra). Among these, most popular treatments have been developed with applications of vasodilative and antiproliferative drugs like nitric oxide (NO), NO-donors, adenosine, calcium channel blockers, endothelin receptor antagonist, phosphodiesterase inhibitors, prostacyclin, prostacyclin analogs, and tyrosine kinase inhibitors (Gessler T, et al., Journal of aerosol medicine and pulmonary drug delivery. 2008; 21(1): 1-12). In particular, tetramethylpyrazine (TMP) (also known as Ligustrazine) is an active alkaloid contained in the rhizome of *Ligusticum chuanxiong* Hort, an herb that has been used for many years in China as an intravenous (i.v) infusion solution for the treatment of occlusive cerebral arteriolar disease (Kwan C Y. Stem Cells. 1994; 12(1):64-67 and PAH (Kwan et al, supara; Chang et al., Journal of pharmacy and pharmacology. 1998; 50(8):881-884). It is a vasodilator and also has antiproliferative and anticoagulant effects. Its mechanism of action includes calcium channel antagonism, cAMP production, and endothelium-dependent NO-mediated relaxation (Chang et al., supra). Furthermore, it has been reported that TMP can significantly decrease pulmonary hypertension caused by acute and chronic hypoxia in rats and ferrets in ex vivo isolated perfused lung model (Cai Y, et al., Proceedings of the Chinese Academy of Medical Sciences and the Peking Union Medical College 1988; 4(3):147-152; Oddoy A, et al., European Respiratory Journal. 1991; 4(10):1223-1227). TMP is also shown to possess neuroprotective (Li S Y, et al., Free radical biology & medicine. Feb. 15, 2010; 48(4):597-608; Tan F, et al., Experimental and therapeutic medicine. May 2015; 9(5): 1757-1762) and anti-platelet functions (Wang Y, et al., Environmental toxicology and pharmacology. July 2016; 45:334-339).

Although vasodilators and antiproliferative agents such as TMP have been used extensively to treat pulmonary hypertension, adverse side effects such as systemic hypotension restrict its clinical use (Liu S et al., European journal of pharmacology. 1990; 191(3):345-350). This is due to the systemic administration of the drug as an i.v infusion. Hence, a fitting response to this problem will be to deliver the drug locally to the airways and alveoli. Particularly in this scenario, where i.v drug administration causes a systemic high concentration in a short period of time leading to adverse side effect, localized pulmonary delivery will require a reduced amount of drug to bring about the same therapeutic response (Meenach S A, et al., 2014 supra; Olschewski H, et al., The New England journal of medicine. Aug. 1, 2002; 347(5):322-329). The only available local delivery for PH is inhaled Iloprost (Ventavis®), delivering the aerosol through I-neb nebulizer system. Approved by FDA in 2004, Iloprost is used to treat both adult and pediatric population (Tissot C, et al., Vascular health and risk management. 2009; 5(1):325-331). For treatment with Iloprost, it is required to administer (nebulize) the solution for 10-15 minutes to obtain the sufficient adult dose. This is typically performed in a clinical setting or hospital, restricting the mobility of the patients.

Thus, improved methods of delivering agents to the lung for treatment of pulmonary hypertension such as PAH are needed.

SUMMARY

Pulmonary drug delivery of dry powder aerosol offers many advantages such as a large surface area for high drug absorption (Mansour H M, et al., Int J Nanomedicine. 2009; 4:299-319; Muralidharan P, et al., Pharmaceutics. 2014; 6(2):333-353; Muralidharan P, et al., Nanomedicine: Nanotechnology, Biology and Medicine. 2015; 11(5):1189-1199), a rapid onset of therapeutic action (Meenach S A, et al., 2014 supra; Olschewski et al., supra; Tissot et al., supra; Mansour et al., supra; Muralidharan et al., 2014, supra; Muralidharan et al., 2015, supra; Xu Z, et al., Journal of Adhesion Science and Technology. 2011; 25(4-5):451-482), low enzymatic activity (Muralidharan et al., 2014, supra; Muralidharan et al., 2015; Stocke N A, et al., International journal of pharmaceutics. 2015; 479(2):320-328), extensive blood supply (Mansour H M, et al., Lipids in Nanotechnology: American Oil Chemists Society Press, Chicago, Ill.; 2011:221-268), avoidance of first-pass metabolism (Mansour et al., 2009, supra; Muralidharan et al., 2014, supra; Mansour et al., 2011, supra), reduced dosing frequency (Muralidharan et al., 2014, supra), and reduced side effects (Mansour et al., 2015, supra; Mansour et al., 2011, supra).

However, prior to the present invention, such delivery of TMP was not possible. Provided herein for the first time is a high-throughput advanced engineering method to develop TMP inhalable particles for local delivery to the lungs as DPIs. The systematic physicochemical characterization indicates that spray drying caused a polymorphic conversion of TMP, which didn't affect the biological response. The outcome from in vitro aerosol performance study shows aerosol dispersion of TMP in a dry powder formulation. The in vitro cellular studies demonstrated the safety of this spray dried formulation. The in vivo inhalation rodent study confirmed that inhaled TMP is efficacious in the attenuation of PH.

Accordingly, provided herein is a composition comprising a polymorphic conversion of a crystal of tetramethylpyrazine (TMP) and optionally a pharmaceutically acceptable carrier (e.g., as a molecular mixture). In some embodiments, the pharmaceutically acceptable carrier is a sugar (e.g., D-mannitol). In some embodiments, the TMP and D-mannitol are present at a molar ratio of 75:25 to 25:75 TMP:D-mannitol. In some embodiments, the composition is a dry powder. In some embodiments, the dry powder is spray dried. In some embodiments, the TMP lacks x-ray diffraction peaks in the 2θ region of 30-60°. In some embodiments, the TMP crystals have a diameter of 0.8-1.5 μm. In some embodiments, TMP compositions are lactose carrier-free. In some embodiments, the compositions have higher aerosol dispersion parameters than existing formulations. In some embodiments, the TMP crystals are generated by a method, comprising: a) preparing a first solution comprising said TMP in an organic solvent; and b) spraying the first solution using a spray drying apparatus. In some embodiments, the method further comprises the steps of preparing a second solution comprising said pharmaceutically acceptable carrier in an organic solvent; and co-spraying the first and second solutions. In some embodiments, the organic solvent is methanol.

Additional embodiments provide a system, comprising: the TMP compositions described herein; and a dry powder inhaler device.

Further embodiments provide a method of treating pulmonary arterial hypertension (PAH) in a subject, comprising: administering the TMP compositions described herein to a subject diagnosed with or having signs or symptoms of PAH under conditions such that the signs or symptoms are reduced. In some embodiments, the signs or symptoms of PAH include a pulmonary arterial pressure of greater than or equal to 22 mmHg at rest of 30 mmHg during exercise. In some embodiments, the method further comprises administering an additional treatment for PAH (e.g., including but not limited to, a vasodilator, an anticoagulant, an antiplatelet agent, an anti-inflammatory agent, or a vascular-remodeling therapy). In some embodiments, the composition is administered to the lung of the subject using a dry powder inhaler.

Still further embodiments provide the use of the TMP compositions described herein to treat PAH in a subject diagnosed with or having signs or symptoms of PAH.

Yet other embodiments provide the TMP compositions described herein for use in treating PAH in a subject diagnosed with or having signs or symptoms of PAH.

Also provided herein is a method of administering TMP to the lung of a subject, comprising: delivering the TMP compositions described herein to the lung of a subject using a dry powder inhaler. In some embodiments, the delivering treats a disease or disorder selected from, for example, acute lung injury (ALI), acute respiratory distress syndrome (ARDS), occlusive cerebral arteriolar disease, a neurological disease, or a platelet disease.

Additional embodiments are described herein.

DEFINITIONS

Figure 1:
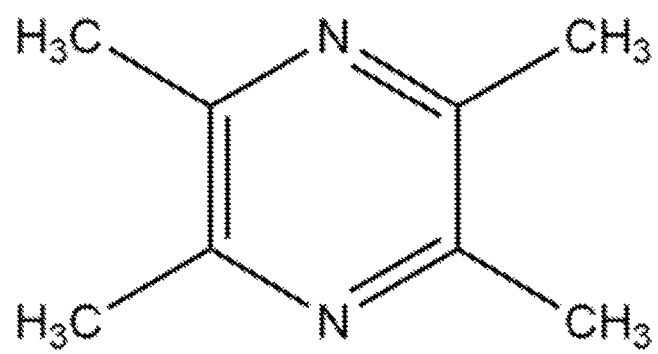
FIG. 1: Chemical Structure of tetramethylpyrazine.

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human or non-human mammal subject.

As used herein, the term "diagnosed," as used herein, refers to the recognition of a disease by its signs and symptoms (e.g., resistance to conventional therapies), or genetic analysis, pathological analysis, histological analysis, and the like.

As used herein, the term "effective amount" refers to the amount of a compound (e.g., a compound of the present disclosure) sufficient to effect beneficial or desired results. An effective amount can be administered in one or more administrations, applications or dosages and is not limited to a particular formulation or administration route.

As used herein, the term "co-administration" refers to the administration of at least two agent(s) (e.g., a compound of the present disclosure) or therapies to a subject. In some embodiments, the co-administration of two or more agents/therapies is concurrent. In some embodiments, a first agent/therapy is administered prior to a second agent/therapy. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

As used herein, the term "pharmaceutical composition" refers to the combination of an active agent with a carrier, inert or active, making the composition especially suitable for diagnostic or therapeutic use in vivo, in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa., (1975)).

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water and industrial samples. Such examples are not however to be construed as limiting the sample types applicable to the present disclosure.

As used herein, the terms "purified" or "to purify" refer, to the removal of undesired components from a sample. As used herein, the term "substantially purified" refers to molecules that are at least 60% free, at least 65% free, at least 70% free, at least 75% free, at least 80% free, at least 85% free, at least 90% free, at least 95% free, at least 96% free, at least 97% free, at least 98% free, at least 99% free, or 100% free from other components with which they usually associated.

As used herein, the term "modulate" refers to the activity of a compound (e.g., a compound of the present disclosure) to affect (e.g., to promote or retard) an aspect of cellular function.

As used herein, the phrase "in need thereof" means that the subject has been identified as having a need for the particular method or treatment. In some embodiments, the identification can be by any means of diagnosis. In any of the methods and treatments described herein, the subject can be in need thereof. In some embodiments, the subject is in an environment or will be traveling to an environment in which a particular disease, disorder, condition, or injury is prevalent.

DETAILED DESCRIPTION

The present invention solves the long unmet need for pulmonary delivery of tetramethylpyrazine (TMP). Pulmonary delivery allows for delivery of high local concentrations of therapeutic agent with toxicity associated with systemic delivery.

In some embodiments, the TMP is a polymorphic conversion of a crystal of TMP. As described herein, in some embodiments, the TMP lacks x-ray diffraction peaks in the 2θ region of 30-60°, which is indicative of a polymorphic conversion.

In some embodiments, TMP is present in a dry powder generated by spray drying (See e.g., below and Jain et al., Research J. Pharma. Dosage Forms and Tech. 2011; 4(2): 74-79). In some embodiments, TMP is spray dried alone or with a pharmaceutically acceptable carrier. In some embodiments, the pharmaceutically acceptable carrier is a sugar (e.g., D-mannitol, lactose, or xylitol). In some embodiments, the TMP and D-mannitol are present at a molar ratio of 75:5 to 25:75 TMP:D-mannitol. In some embodiments, after drying, the TMP crystals have a diameter of 0.8-1.5 µm.

Generally, during spray-drying, heat from a hot gas such as heated air or nitrogen is used to evaporate a solvent from droplets formed by atomizing a continuous liquid feed. If desired, the spray drying or other instruments, e.g., jet milling instrument, used to prepare the dry particles can include an inline geometric particle sizer that determines a geometric diameter of the respirable dry particles as they are being produced, and/or an inline aerodynamic particle sizer that determines the aerodynamic diameter of the respirable dry particles as they are being produced.

For spray drying, solutions, emulsions or suspensions that contain the components of the dry particles to be produced in a suitable solvent (e.g., aqueous solvent, organic solvent, aqueous-organic mixture or emulsion) are distributed to a drying vessel via an atomization device. For example, a nozzle or a rotary atomizer may be used to distribute the solution or suspension to the drying vessel. For example, a rotary atomizer having a 4- or 24-vaned wheel may be used. Examples of suitable spray dryers that can be outfitted with either a rotary atomizer or a nozzle, include, Mobile Minor Spray Dryer or the Model PSD-1, both manufactured by GEA Group (Niro, Inc.; Denmark). Actual spray drying conditions will vary depending, in part, on the composition of the spray drying solution or suspension and material flow rates. The person of ordinary skill will be able to determine appropriate conditions based on the compositions of the solution, emulsion or suspension to be spray dried, the desired particle properties and other factors. In general, the inlet temperature to the spray dryer is about 90° C. to about 300° C. The spray dryer outlet temperature will vary depending upon such factors as the feed temperature and the properties of the materials being dried. Generally, the outlet temperature is about 50° C. to about 150° C. The spray dryer outlet temperature will vary depending upon such factors as the feed temperature and the properties of the materials being dried. Generally, the outlet temperature is about 50° C. to about 150° C.

A nitrogen source with a specified moisture level may be flown over, across, or through the dry powder to add a specific moisture content to the dry powder. Such moisture can provide the desired working density of the powder. Spray drying methods in accordance with the invention are described in the Examples herein and in U.S. Pat. Nos. 6,848,197 and 8,197,845, incorporated herein by reference.

If desired, the respirable dry particles that are produced can be fractionated by volumetric size, for example, using a sieve, or fractioned by aerodynamic size, for example, using a cyclone, and/or further separated according to density using techniques known to those of skill in the art.

In some embodiments, the TMP crystals are generated by a method, comprising: a) preparing a first solution comprising said TMP in an organic solvent; and b) spraying the first solution using a spray drying apparatus. In some embodiments, the method further comprises the steps of preparing a second solution comprising said pharmaceutically acceptable carrier in an organic solvent; and co-spraying the first and second solutions. In some embodiments, the organic solvent is methanol.

Administration to the respiratory tract may also be achieved by means of an aerosol formulation in which the active ingredient is provided in a pressurized pack with a suitable propellant. If the compounds or pharmaceutical compositions comprising them are administered as aerosols, for example as nasal aerosols or by inhalation, this can be carried out, for example, using a spray, a nebulizer, a pump nebulizer, an inhalation apparatus, a metered inhaler or a dry powder inhaler. Pharmaceutical forms for administration of the compounds as an aerosol can be prepared by processes well known to the person skilled in the art. For their preparation, for example, solutions or dispersions of the compounds in water, water/alcohol mixtures or suitable saline solutions can be employed using customary additives, for example benzyl alcohol or other suitable preservatives, absorption enhancers for increasing the bioavailability, solubilizers, dispersants and others and, if appropriate, customary propellants, for example include carbon dioxide, CFCs, such as, dichlorodifluoromethane, trichlorofluoromethane, or dichlorotetrafluoroethane; and the like. The aerosol may conveniently also contain a surfactant such as lecithin. The dose of drug may be controlled by provision of a metered valve.

In formulations intended for administration to the respiratory tract, including intranasal formulations, the compound will generally have a small particle size for example of the order of 50 microns or less. Such a particle size may be obtained by means known in the art, for example by micronization. When desired, formulations adapted to give sustained release of the active ingredient may be employed.

Alternatively the active ingredients may be provided in the form of a dry powder, for example, a powder mix of the compound in a suitable powder base such as lactose, starch, starch derivatives such as hydroxypropylmethyl cellulose and polyvinylpyrrolidone (PVP).

The compounds may optionally exist as pharmaceutically acceptable salts including pharmaceutically acceptable acid addition salts prepared from pharmaceutically acceptable non-toxic acids including inorganic and organic acids. Representative acids include, but are not limited to, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like. Certain pharmaceutically acceptable salts are listed in Berge, et al., Journal of Pharmaceutical Sciences, 66:1-19 (1977), incorporated herein by reference in its entirety.

Additional embodiments provide a system, comprising: the TMP compositions described herein; and a dry powder inhaler device (e.g., commercially available devices). The inhaler may be a single dose or multi-dose inhaler.

In one aspect of this invention, an inhaler is a dry powder inhaler. A variety of inhalers can be used including the Aerolizer, Diskus, Flexhaler, Handihaler, Neohaler, Pressair, Rotahaler, Turbohaler, and Twisthaler. Other dry powder inhalers which can be used are described in U.S. Pat. Nos. 6,766,799, 7,278,425 and 8,496,002, each of which are hereby incorporated in by reference for their disclosure relating to the inhalation devices described therein. In one aspect of the invention, the compartment is a capsule or a blister pack. In one aspect of the invention, the inhaler has a resistance of about 0.05 to about 0.25, about 0.15 to about 0.25, 0.05 to about 0.15, 0.2 to about 0.25, or about 0.2. Resistance as referred herein is measured in: Square root of $CmH_2O$/Liters 20 per minute. Gravimetric analysis, using Cascade impactors, is a method of measuring the size distribution of airborne particles. Another method for measuring the size distribution of airborne particles is the Multi-stage liquid Impinger (MSLI). The MSLI is used to provide an indication of the flow rate dependence of the powder.

As used herein, the term "nominal powder dose" is the total amount of powder held in a capsule. As used herein, the term "nominal drug dose" is the total amount of TMP contained in the nominal powder dose. The nominal powder dose is related to the nominal drug dose by the load percent of drug in the powder.

Tap density can be measured by using instruments known to those skilled in the art such as the Dual Platform Microprocessor Controlled Tap Density Tester (Vankel, N.C.) or a GEOPYC™ instrument (Micrometries Instrument Corp., Norcross, Ga., 30093). Tap density is a standard measure of the envelope mass density. Tap density can be determined using the method of USP Bulk Density and Tapped Density, United States Pharmacopia convention, Rockville, Md., 10th Supplement, 4950-4951, 1999. Features which can contribute to low tap density include irregular surface texture and porous structure. The envelope mass density of an isotropic particle is defined as the mass of the particle divided by the minimum sphere envelope volume within which it can be enclosed.

The diameter of the spray-dried particles, for example, the VMGD, can be measured using a laser diffraction instrument (for example Helos, manufactured by Sympatec, Princeton, N.J.). Other instruments for measuring particle diameter are well known in the art.

In some embodiments, the inhalable powder comprising TMP as described above is used to fill capsules suitable for use in an inhaler. The term "capsule material" as used herein refers to the material from which the shell of the capsule for inhalation is made. In one embodiment, the capsule material according to the invention is selected from among gelatin, cellulose derivatives, starch, starch derivatives, chitosan and synthetic plastics. If gelatin is used as the capsule material, examples according to the invention may be selected from among polyethyleneglycol (PEG), PEG 3350, glycerol, sorbitol, propyleneglycol, PEO-PPO block copolymers and other polyalcohols and polyethers. If cellulose derivatives are used as the capsule material, examples according to the invention may be selected from hydroxypropylmethylcellulose (HPMC), hydroxypropylcellulose, methylcellulose, hydroxymethylcellulose and hydroxyethylcellulose. If synthetic plastics are used as the capsule material, examples according to the invention may be selected from polyethylene, polycarbonate, polyester, polypropylene and polyethylene terephthalate. In one embodiment, the capsule material further comprises titanium dioxide. In one preferred embodiment the capsule comprises HPMC and titanium dioxide. In one embodiment, the capsule comprises carrageenan. In a further embodiment, the capsule comprises potassium chloride. In a still further embodiment, the capsule comprises, HPMC, carrageenan, potassium chloride, and titanium dioxide. In one embodiment, the capsule size is selected from 000, 00, 0, 1, or 2.

In one aspect of the invention, the powders have low electrostatic charge to enable high dispersion from the capsule. The capsules of the invention are particularly suitable for use in a dry powder inhaler for the delivery of a dry powder composition comprising an effective amount of TMP to a patient in need thereof for example, for treating pulmonary disease.

The present invention provided methods of administering TMP to the lung for any use (e.g., treatment of diseases currently treated with TMP such as PAH or other disorders not currently treated by TMP.

Further embodiments provide a method of treating pulmonary arterial hypertension (PAH) in a subject, comprising: administering the TMP compositions described herein to a subject diagnosed with or having signs or symptoms of PAH under conditions such that the signs or symptoms are reduced. In some embodiments, the signs or symptoms of PAH include a pulmonary arterial pressure of greater than or equal to 22 mmHg at rest of 30 mmHg during exercise. In some embodiments, the method further comprises administering an additional treatment for PAH (e.g., including but not limited to, a vasodilator, an anticoagulant, an antiplatelet agent, an anti-inflammatory agent, or a vascular-remodeling therapy). In some embodiments, the composition s administered to the lung of the subject using a dry powder inhaler.

Still further embodiments provide the use of the TMP compositions described herein to treat PAH in a subject diagnosed with or having signs or symptoms of PAH.

Yet other embodiments provide the TMP compositions described herein for use in treating PAH in a subject diagnosed with or having signs or symptoms of PAH.

Also provided herein is a method of administering TMP to the lung of a subject, comprising: delivering the TMP compositions described herein to the lung of a subject using a dry powder inhaler. In some embodiments, the delivering treats a disease or disorder selected from, for example, occlusive cerebral arteriolar disease, a neurological disease, acute lung injury (ALI), acute respiratory distress syndrome (ARDS), or a platelet disease.

EXPERIMENTAL

Example 1

Experimental: Materials and Methods
Materials

TMP [≥98% purity] [$C_8H_{12}N_2$; molecular weight (MW): 136.19], shown in FIG. 1 (ChemDraw Ultra Ver. 10.0; CambridgeSoft, Cambridge, Mass.), was obtained from Sigma-Aldrich (St. Louis, Mo.). Methanol (HPLC grade, ACS-certified grade, purity 99.9%) was obtained from Fisher Scientific (Fair Lawn, N.J.). HYDRANAL®-Coulomat AD was from Sigma-Aldrich. Resazurin sodium salt was obtained from ACROS Organics. DMSO LC-MS grade was from Thermo Scientific. The nitrogen gas used was ultra-high purity (UHP) (Cryogenics and gas facility, The University of Arizona, Tucson, Ariz.). Pulmonary cell lines for cellular studies were purchased from the American Type Culture Collection ATCC® A549 (ATCC® CCL-85™), H358 (ATCC® CRL-5807™) and Calu-3 (ATCC® HTB-55™). A549 and H358 were grown in Dulbecco's modified Eagle's medium (DMEM) Advanced 1X supplemented with Fetal Bovine Serum (FBS), Pen-Strep, Fungizone®, and L-Glutamine obtained from Gibco® by Life Technologies (Thermo Fisher Scientific Inc, USA). Calu-3 cell line was grown Eagle's minimum essential medium (EMEM) obtained from ATCC supplemented with FBS, Pen-Strep and fungizone obtained from Gibco® by Life Technologies (Thermo Fisher Scientific Inc, USA).

Methods

Advanced Close Mode Spray Drying from Organic Solution

Spray drying (SD) was carried out using a B-290 Buchi Mini Spray Dryer coupled with a B-295 Inert Loop and high-performance cyclone (Buchi Labortechnik AG, Switzerland) in a closed mode using compressed UHP dry nitrogen as the atomizing gas. The feed solution was prepared by dissolving the 1% w/v drug in methanol. A stainless steel nozzle with a diameter of 0.7 mm was used to atomize the drug solution. All spray dried particles were separated from the via high-performance cyclone and collected into glass sample collector. The following conditions were used: atomization gas flow rate 670 l h$^{-1}$ (55 mm), aspirator rate of 38 m$^3$ h$^{-1}$ (100%), the inlet temperature of 100° C. and feed rate of 27 ml min$^{-1}$. Spray dried powder was stored in desiccated condition at −20° C. until further analysis.

Scanning Electron Microscopy

Using similar conditions reported by previous authors (Meenach S A, et al., AAPS PharmSciTech. 2014; 15(6): 1574-1587; Muralidharan P, et al., Molecular Systems Design & Engineering. 2016), the shape and surface morphology of particles were evaluated by scanning electron microscopy (SEM), using a SEM FEI Inspect S (Brno, Czech Republic). Samples were placed on a double coated carbon conductive adhesive Pelco Tabs™ (TedPella Inc., Redding, Calif., USA), which were adhered to aluminum stubs (TedPella Inc., Redding, Calif., USA). Samples were coated with a gold thin film using a Hummer 6.2 sputtering system from Anatech (Union City, Calif.). The coating process was operated at 15 AC milliAmperes with about 7 kV of voltage for 1.5 minutes. The electron beam with an accelerating voltage of 30 kV was used at a working distance of 9-12.5 mm. Several magnification levels were used for image capture.

Laser Diffraction Particle Sizing and Size Distribution

Particle size and size distributions of the particles were determined by laser diffraction with the SALD-7101 (Shimadzu Scientific Instruments, Japan) using conditions previously reported (Li X, Mansour H M., AAPS PharmSciTech. December 2011; 12(4):1420-1430; Meenach S A, et al., Int J Nanomedicine. 2013; 8:275-293; Wu X, et al., Drug design, development and therapy. 2013; 7:59-72; Wu X, et al., Int J Nanomedicine. 2013; 8:1269-1283) for measurement of the mean size and size distribution of SD particles in aqueous suspension. Samples were dispersed in ultrapure water and ultrasonicated for 10 s in water bath ultrasonicator Branson 7500 before measuring particle size. Sample particle dispersion was immediately transferred to particle size measuring cell and kept stirring during measurement in nano particle size analyzer. The low refractive index of 1.50-0.00i was used. Volume-based measurements were obtained. $D_{V10}$, $D_{V50}$, and $D_{V90}$ were used as particle size characterization parameters. The span value was calculated using the equation defined as $$\text{Span} = [(DV_{90} - DV_{10})/DV_{50}] \quad \text{Equation 1.}$$

X-Ray Powder Diffraction (XRPD)

Using similar conditions reported by previous authors (Meenach S A, et al., AAPS PharmSciTech. 2014; 15(6): 1574-1587; Muralidharan P, et al., Molecular Systems Design & Engineering. 2016), X-ray powder diffraction (XRPD) patterns of samples were collected at room temperature with a PanAnalytical X'pert diffractometer (PANalytical Inc., Westborough, Mass., USA) with Cu Kα radiation (45 kV, 40 mA, and λ=1.5406 Å) between 8.0° and 80.0° (2θ) with a scan rate of 2.00° per minute at ambient temperature. The powder samples were loaded on zero-background silicon wafer sample holder and diffraction was measured with X'celerator detector.

Differential Scanning Calorimetry (DSC)

Thermal analysis and phase transitions measurements were performed using a TA Q2000 differential scanning calorimeter (DSC) (TA Instruments, New Castle, Del.) equipped with T-Zero® technology, and RSC90 automated cooling system. Approximately a mass of 1-3 mg of powder was weighed into a hermetic anodized aluminum T-Zero® DSC pan. These were hermetically sealed with a T-Zero hermetic press (TA Instruments). An empty hermetically sealed pan was used as reference pan. UHP nitrogen gas was used at a rate of 50 mL min$^{-1}$. All samples were heated starting at 0° C. to 150° C. at a scanning rate of 5.00° C. min$^{-1}$. All measurements were done in triplicate.

Hot-Stage Microscopy (HSM) Under Cross-Polarizers

Using similar conditions reported by previous authors (Meenach S A, et al., AAPS PharmSciTech. 2014; 15(6): 1574-1587; Muralidharan P, et al., Molecular Systems Design & Engineering. 2016), hot-stage microscopy (HSM) was performed using a Leica DMLP cross-polarized microscope (Wetzlar, Germany) equipped with a Mettler FP 80 central processor heating unit and Mettler FP82 hot stage (Columbus, Ohio, USA). Samples were mounted on a cover glass slide and heated from 25.0° C. to 100.0° C. at a heating rate of 5.00° C. min$^{-1}$. The images were digitally captured using a Nikon Coolpix 8800 digital camera (Nikon, Tokyo, Japan) under 10× optical objective and 10× digital zoom.

Karl Fisher Coulometric Titration

The residual water content of spray dried powder was analytically quantified by Karl Fischer (KF) coulometric titration, using a TitroLine® 7500 KF trace coupled with a TM 235 (SI Analytics GmbH, Mainz, Germany). Approximately 1-10 mg of powder was added directly into the reaction cell that contained HYDRANAL® coulomat AD reagent.

Confocal Raman Microspectroscopy (CRM) and Chemical Imaging

Microspectroscopic component analysis of DPI formulations was carried by the noninvasive and nondestructive Raman spectroscopy. Using similar conditions previously reported (Meenach S A, et al., AAPS PharmSciTech. 2014; 15(6):1574-1587; Muralidharan P, et al., Molecular Systems Design & Engineering. 2016; Li X, Vogt F G, Hayes D, Mansour H M. Physicochemical characterization and aerosol dispersion performance of organic solution advanced spray-dried microparticulate/nanoparticulate antibiotic dry powders of tobramycin and azithromycin for pulmonary inhalation aerosol delivery. European Journal of Pharmaceutical Sciences. 2014; 52:191-205; Meenach S A, et al., European Journal of Pharmaceutical Sciences. 2013; 49(4): 699-711), Raman spectra was obtained at 514 nm laser excitation using Renishaw InVia Reflex (Gloucestershire, UK) at the surface using a 20× magnification objective on a Leica DM2700 optical microscope (Wetzlar, Germany) and equipped with a Renishaw inVia Raman system (Gloucestershire, UK). This Renishaw system has a 2400l/mm grating, with a slit width of 65 μm and a thermoelectrically cooled Master Renishaw CCD detector. The laser power was adjusted to achieve 5000 counts per second for the 520 cm$^{-1}$ line of the internal Si Reference. Raman spectra was achieved using varying laser power (10-100%), and 10 seconds of exposure time.

In Vitro Aerosol Dispersion Performance

In accordance with US Pharmacopeia (USP) Chapter <601> specification on aerosols and using conditions similar to previously reported (Meenach S A, et al., AAPS PharmSciTech. 2014; 15(6):1574-1587; Muralidharan P, et al., Molecular Systems Design & Engineering. 2016), the in vitro aerosol dispersion properties of the dry powder particles were determined using the Next Generation Impactor® (NGI®) with a stainless steel induction port (USP throat) attachment (NGI® Model 170), equipped with specialized stainless steel NGI® gravimetric insert cups (MSP Corporation, Shoreview, Md., USA). The NGI® was coupled with a Copley TPK 2000 critical flow controller connected to a Copley HCP5 vacuum pump, and the airflow rate (Q), was measured and adjusted prior to each experiment using a Copley DFM 200 flow meter (Copley Scientific, UK).

The mass of powder deposited on each stage was quantified by a gravimetric method using type A/E glass fiber filters with diameter 55 mm (PALL Corporation, Port Washington, N.Y.) and 75 mm (Advance, Japan). Quali-V clear HPMC size 3 inhalation grade capsules (Qualicaps, North Carolina) filled with about 10 mg of powder were used. Three capsules were used in each experiment. In vitro aerosolization was done in triplicate (n=3) under ambient conditions. The NGI™ was operated at a flow rate of 601 min¹ with an actuation time of 10 s through the inhaler. The glass fiber filter was measured gravimetrically before and after actuation, on each stage, to determine the particle stage deposition. The fine particle dose (FPD), fine particle fraction (FPF), respirable fraction (RF), and emitted dose (ED) were calculated using the following equations:

$$\text{Fine particle fraction}(FPF) = \frac{\text{Fine particle dose}}{\text{Initial particle mass loaded in capsules}} \times 100\% \quad \text{Equation 3}$$

$$\text{Respirable fraction}(RF) = \frac{\text{Fine particle dose}}{\text{Total particle mass on all stages}} \times 100\% \quad \text{Equation 4}$$

$$\text{Emitted dose}(ED) = \frac{\text{Initial mass in capsules} - \text{Final mass remaining in capsules}}{\text{Initial mass in capsules}} \times 100\% \quad \text{Equation 5}$$

The mass mean aerodynamic diameter (MMAD) and geometric standard deviation (GSD) of aerosol dispersion profiles were determined using a Mathematica (Wolfram Research Inc., Champaign, Ill.) program ((Meenach S A, et al., AAPS PharmSciTech. 2014; 15(6):1574-1587; Muralidharan P, et al., Molecular Systems Design & Engineering. 2016). The aerosol dispersion performance was tested using three FDA approved inhalers Handihaler®, Aerolizer®, and Neohaler®.

In Vitro Cell Dose Response Assay

Cell-based assays are often used to determine if test molecules have effects on cell proliferation or show direct cytotoxicity effects that eventually leads to cell death. The effects of TMP formulations were analyzed by measuring the response of lung adenocarcinoma cells at different concentrations of the drug. The A549 pulmonary cell line is a human alveolar epithelial lung adenocarcinoma cell line and has been used as a model of the alveolar type II pneumocyte cell in in vitro pulmonary drug delivery and metabolism studies. The H348 pulmonary cell line is a human bronchoalveolar epithelial cell line similar to alveolar type II cells and express lung surfactant associated protein A (SP-A) (Acosta M F, et al., Current pharmaceutical design. 2016; 22(17):2522-2531). Both cell lines were grown in a growth medium including Dulbecco's modified Eagle's medium (DNEM) advanced 1×, 10% (v/v) fetal bovine serum (FBS), Pen-Strep (100 U ml$^{-1}$ penicillin, 100 µg ml$^{-1}$), Fungizone (0.5 µg ml$^{-1}$ amphotericin B, 0.41 µg ml$^{-1}$ sodium deoxycholate), and 2 mM L-Glutamine in a humidified incubator at 37° C. and 5% $CO_2$.

As previously reported (Acosta et al., 2014, supra), both cell lines were seeded in 96-well plates at 5000 cells/well and 100 µl/well and allowed to attach for 48 hours. Then, the cells were exposed to 100 µl of TMP dissolved in media at different concentrations and incubated for 72 hours after exposure. Continuously, 20 µl of 10 µM resazurin sodium salt dissolved in 1% DMSO in media was added to each well and incubated for 4 hours. At this point, the fluorescence intensity was detected at 544 nm (excitation) and 590 nm (emission) using a Synergy H1 Multi-Mode Reader (BioTek Instruments Inc., Winooski, Vt.). The relative viability of each sample was calculated as follow:

$$\text{Relative viability}(\%) = \frac{\text{Sample fluorescence intensity}}{\text{Control fluorescence intensity}} \times 100\% \quad \text{Equation 6}$$

In Vitro Transepithelial Electrical Resistance Analysis

Calu-3 lung epithelial cells, a human lung adenocarcinoma cell line derived from the bronchial submucosal airway region, were grown in a growth medium including Eagle's minimum essential medium (EMEM), 10% (v/v) fetal bovine serum (FBS), Pen-Strep (100 U ml-1 penicillin, 100 µg ml-1), Fungizone (0.5 µg ml-1 amphotericin B, 0.41 µg ml-1 sodium deoxycholate) in humidified incubator at 37° C. and 5% $CO_2$, as previously reported (Acosta et al., supra; Meenach S A, 2014, supra; Meenach S A, et al., European Journal of Pharmaceutical Sciences. 2013; 49(4): 699-711). The cells were seeded at 500,000 cells/ml in Costar Transwells® (0.4 µm polyester membrane, 12 mm for a 12-well plate) with 0.5 ml of media on the apical side and 1.5 ml of media on the basolateral side. Media was changed every other day from the basolateral and apical side. After 10 days of growth, when the cells reached a TEER value of about 1000 $\Omega/cm^2$ which is an indicator of a confluent monolayer at liquid covered culture (LCC) the media was removed from both sides and 800 µl of media was added to the basolateral side of the Transwells to facilitate air-interface culture (AIC) conditions. The TEER responses of the cells were measured with an Endohom 12 mm Culture Cup (World Precision Instruments, Sarasota, Fla.). For TEER measurement, 0.5 ml of media was added to the apical side of the Transwell 5 min before measurement and then immediately removed to return the cells to AIC conditions. After the TEER values reached 500 $\Omega/cm^2$ (indicating a confluent monolayer at AIC conditions), the cells were exposed to 100 µM of SD TMP and representative co-SD formulations dissolved in non-supplemented EMEM media. The liquid aerosol formulations were delivered to the Calu-3 cells at AIC by using a Penn Century MicroSprayer® Aerolizer—Model IA-1B [1]. TEER values were then recorded for up to 7 days after aerosol treatment, as previously reported (Meenach S A, 2014, supra; Meenach S A, et al., April 2016; 48(4):1701-1709).

In Vivo Hemodynamic Efficacy Studies in PH Induced Rats

In vivo studies were conducted in a monocrotaline (MCT) rat model with the purpose of testing the efficacy of TMP in decreasing PH. A total of 30 male Sprague Dawley rats (280-350 g) were used in this study. Rats were purchased from Charles River Laboratories International Inc. (Wilmington, Mass.). Rats were weighted weekly to monitor their health. PH was induced by injecting 60 mg/kg of MCT via intraperitoneally. The animals were divided into 5 groups (n=5) into the following categories: 1) Naïve (control), 2) Naïve+TMP, 3) MCT (PH induced) 4) MCT+ treated with vehicle (air), 5) MCT+ treated with TMP. Two weeks after MCT administration, the rats started to get the treatment via aerosolization of a dry powder formulation of SD TMP (10 mg/kg) using a Penn Century Dry Powder Insufflator™— Model DP-4M for 14 days. Right ventricle systolic pressure (RVSP) hemodynamics were performed after 2 weeks and 4 weeks after MCT administration by inserting a customized pressure transducer catheter (SPR-513, Millar Instruments, Houston, Tex.), into the right ventricle (RV) via the right jugular vein and right atrium. The transducer was connected to a Millar Transducer Control Unit TC-510 and PL3504 PowerLab 4/35 data acquisition system (ADInstruments, Inc., Colorado Springs, Colo.). At the end of pressure recording, the animals were euthanized.

All animal studies were performed in accordance with Institutional Animal Care & Use Committee (IACUC) Guidelines for the care and use of laboratory animals under the protocol approved by University of Arizona Institutional Animal Care & Use Committee.

Statistical Analysis

All experiments were performed in at least triplicate (n=3) unless otherwise mentioned. All data was statistically analyzed using Sigma Plot 13.0 (Systat Software Inc., San Jose, Calif.). Unpaired student t-test and one-way analysis of variance (ANOVA) was performed to compare the statistical significance of the test groups. P value≤0.050 was considered to be statistically significant.

Results

Scanning Electron Microscopy (SEM)

Figure 2:
FIG. 2: Scanning Electron Micrograph of A) raw TMP and B) SD TMP at 2,000×
Figure 2:
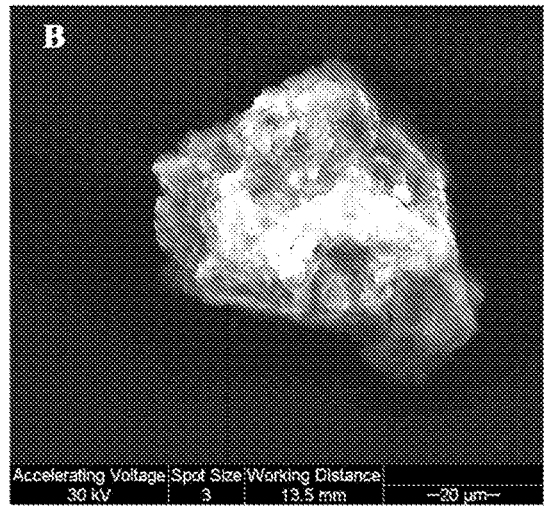

The particle shape and surface morphology were visualized by SEM as shown in FIG. 2 for raw TMP and SD TMP. SD TMP exhibited oblong and pitted morphology compared to raw TMP.

Laser Diffraction Particle Sizing

The particles size distribution from the laser diffraction was found to be between 4-14 μm. The average values of $D_{v10}$, $D_{v50}$ and $D_{v90}$ was found to be 4.186±0.701, 6.156±1.47 and 14.552±4.928 μm respectively. The span value was calculated to be 1.684±0.645.

X-Ray Powder Diffraction (XRPD)

Figure 3:
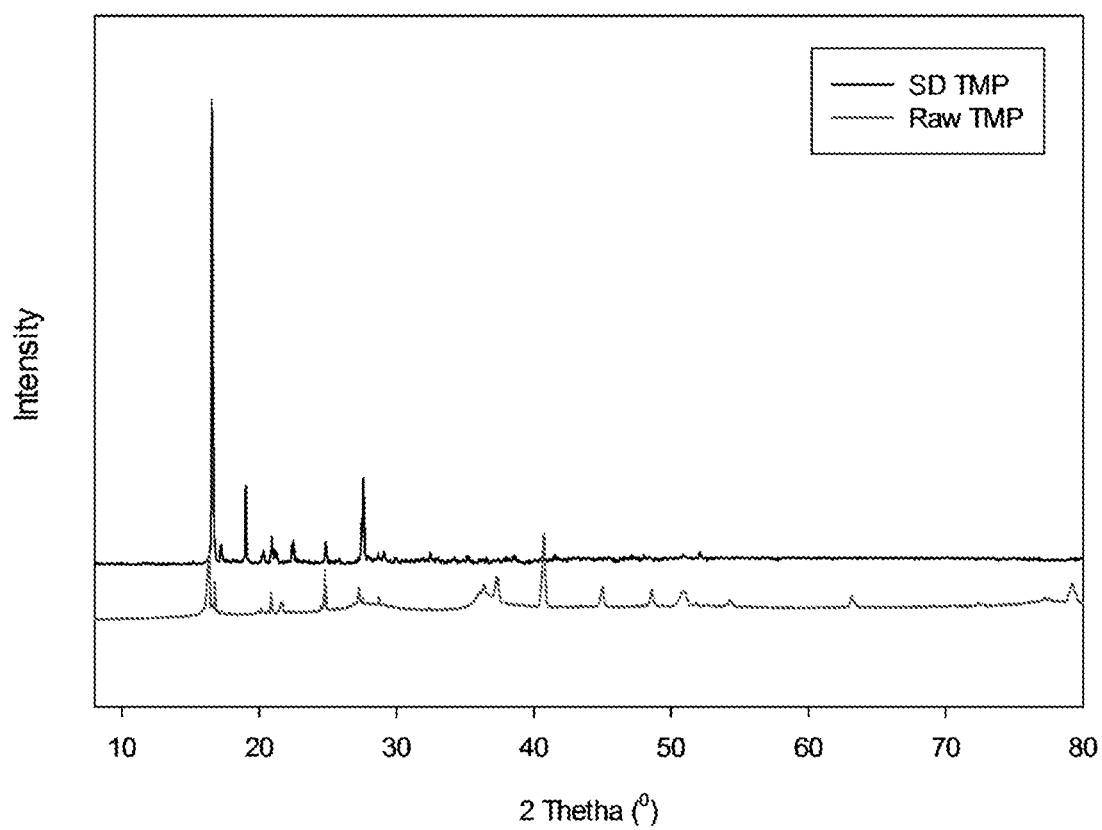
FIG. 3: X-ray Powder Diffractogram of Raw and SD TMP

The XRPD pattern of raw TMP showed sharp and intensive peaks at 2θ values of 16.36°, 24.78°, 36.35°, 37.37°, 40.75°, 45.03°, 48.58° and 50.89° characteristic of long-range molecular order (i.e. crystallinity) as shown in FIG. 3. SD TMP had intensive peaks at 16.56°, 19.00°, 24.83°, and 27.56° indicative of the retention of crystallinity following spray drying. It is notable that the SD TMP particles, unlike raw TMP, didn't exhibit any peak in the 2θ region of 30-60°. This is indicative of a polymorphic conversion of the spray dried TMP from the initial form that was spray dried.

Figure 4:
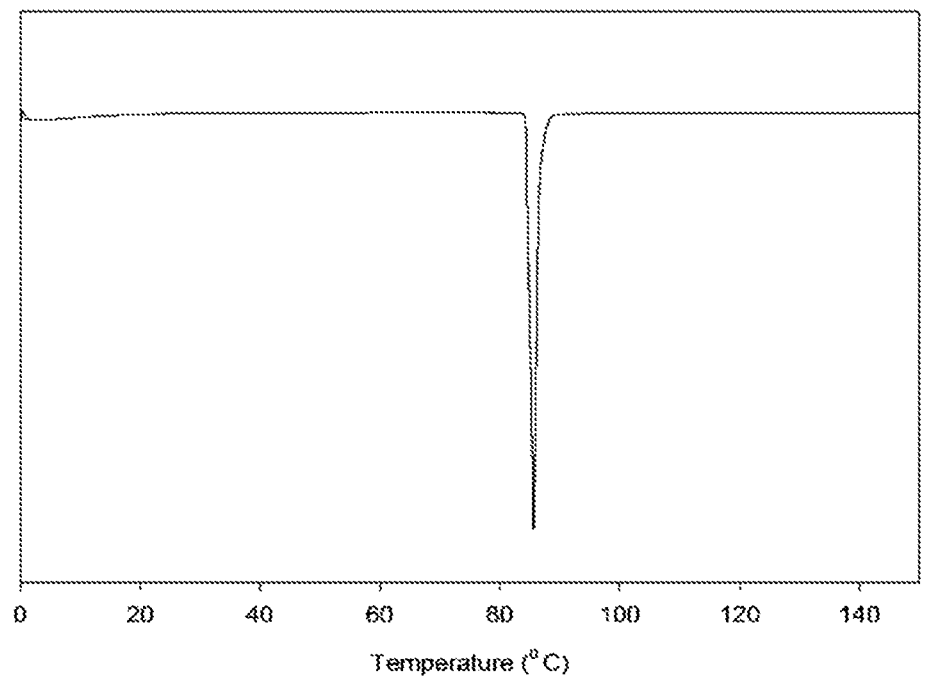
FIG. 4: DSC thermogram of A) Raw TMP and B) SD TMP
Figure 4:
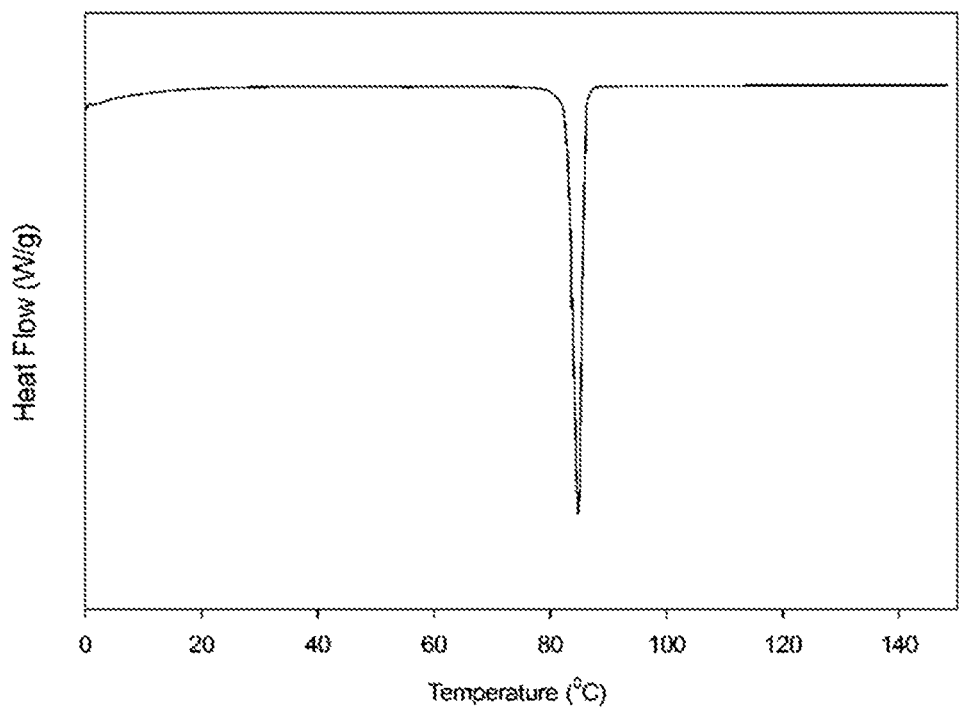

Differential Scanning Calorimetry (DSC) DSC of the raw and spray dried TMP showed in FIG. 4 has a single transition at around 85° C. The single endotherm seen in this thermal analysis indicates that the compound is crystalline with a melting point around 85° C.

Hot-Stage Microscopy Under Cross-Polarizer Lens

Figure 5:
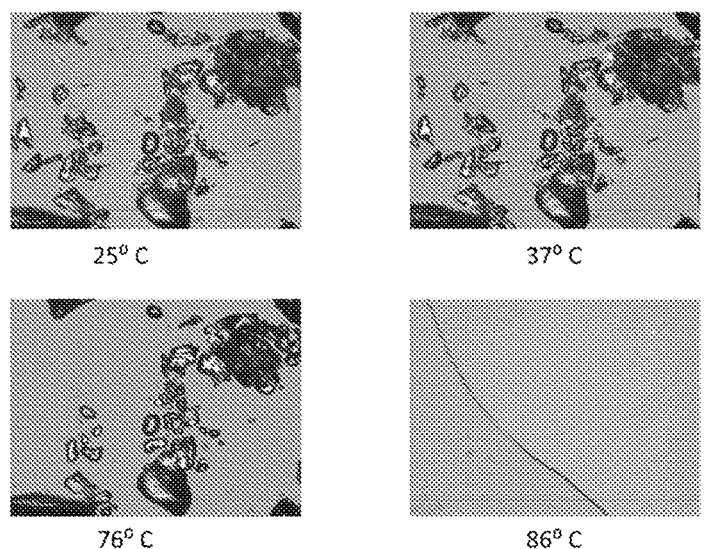
FIG. 5: Hot Stage Micrograph A) Raw TMP and B) SD TMP
Figure 5:
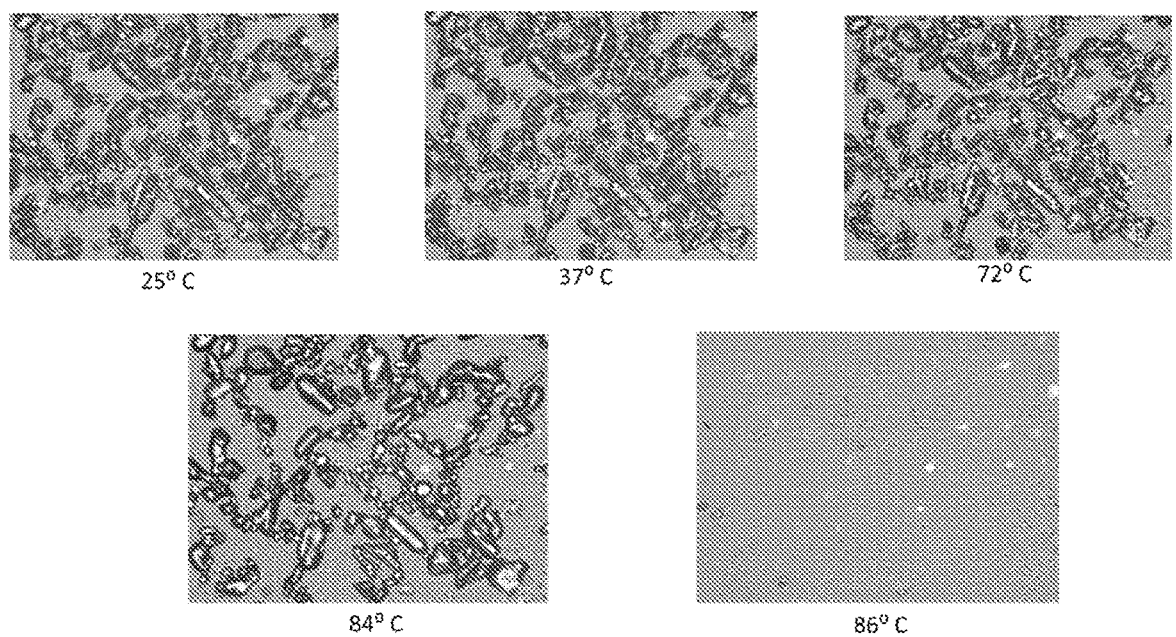

The raw TMP and SD TMP visualized under the cross-polarized light, FIG. 5, exhibits birefringence which is typical of crystals. Upon heating the particles at constant rate, raw TMP particles started melting around 62° C. and completely melted at ~86° C. While the SD TMP particles started melting around 60° C. and completely melted around 86° C. The difference in the melting observed could be due to the difference in the surface property of the particles which is known to be affected following spray drying process. The difference in the polymorphic form of the two particles can contribute to this as well.

Karl Fischer Titration

The residual water content using Karl Fischer titration was quantified as 0.633±0.251% w/w for raw TMP. However, the SD TMP had a little lower water content which was measured as 0.368±0.103% w/w. Table 1 lists the characterization data for Raw and SD TMP.

Confocal Raman Microspectroscopy (CRM) & Chemical Imaging

Figure 6:
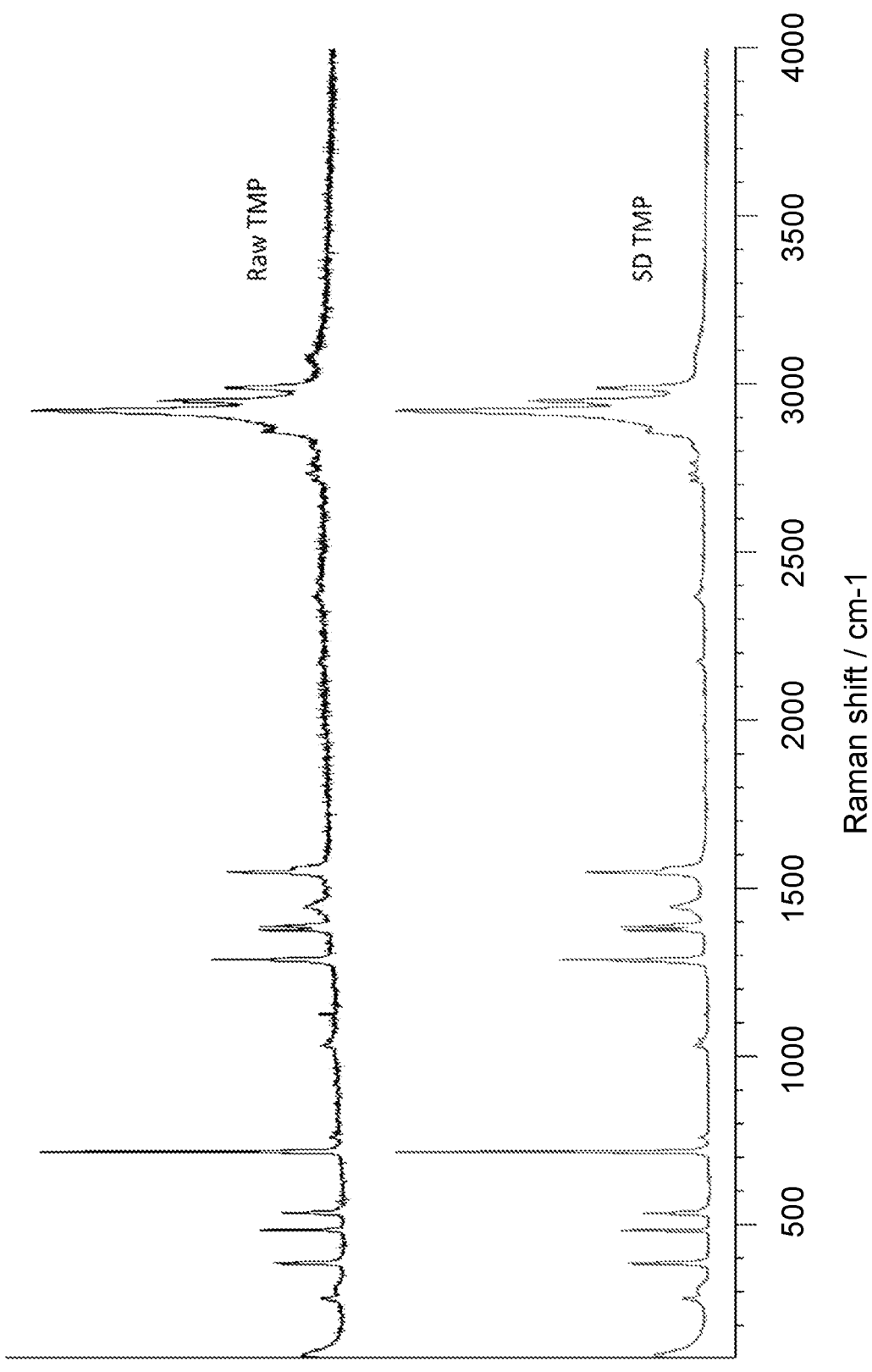
FIG. 6: Raman specta of Raw TMP and SD TMP

From FIG. 6, the Raw and SD TMP have similar spectra indicating that the TMP molecule remained the same before and after spray drying. Prominent peaks were seen at 714 cm$^{-1}$, 1286 cm$^{-1}$, 1547 cm$^{-1}$ and between 2900-3000 cm$^{-1}$ wavenumbers. The sharp peaks seen in this spectra concurs with the inference of TMP crystallinity before and after spray drying.

In Vitro Aerosol Dispersion Performance Via Next Generation Impactor™

Figure 7:
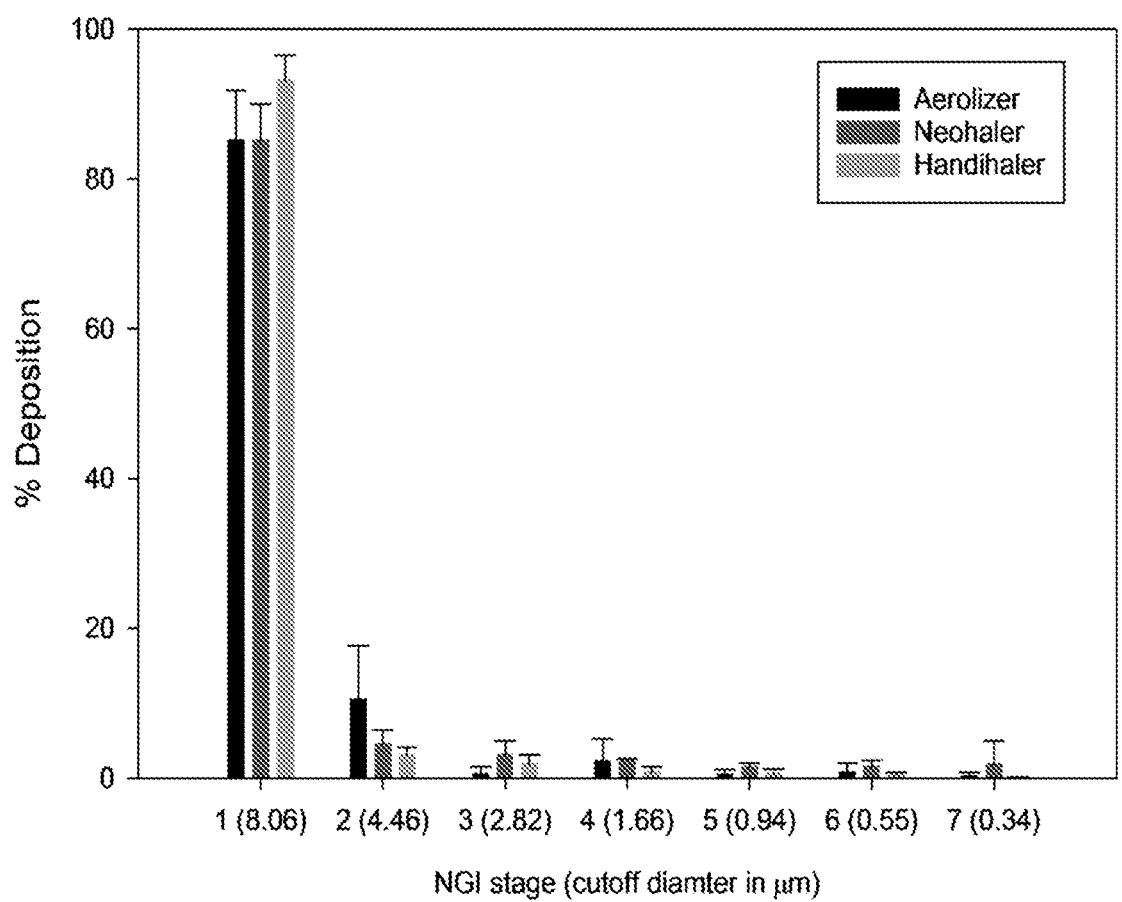
FIG. 7: Aerosol Stage Deposition of SD TMP using NGI® at 60 L min-1 flow rate.

The aerosol dispersion performance of SD TMP using the three inhaler devices is listed in Table 2. The NGI stage deposition using different DPI devices is exhibited in FIG. 7. The emitted dose from the high resistance Handihaler device was 100%, while the other two devices emitted 88% of the loaded powder from the capsules. The fine particle fraction (FPF) was 1.41, 4.36 and 3.33% for Aerolizer®, Neohaler® and Handihaler® respectively. Mass median aerodynamic diameter (MMAD) was found to be 15.23, 43.73 and 68.4 μm using Aerolizer®, Neohaler® and Handihaler® respectively. In general, the MMAD was better with the lower resistance device Aerolizer®.

In Vitro Cell Dose-Response Assay

Figure 8:
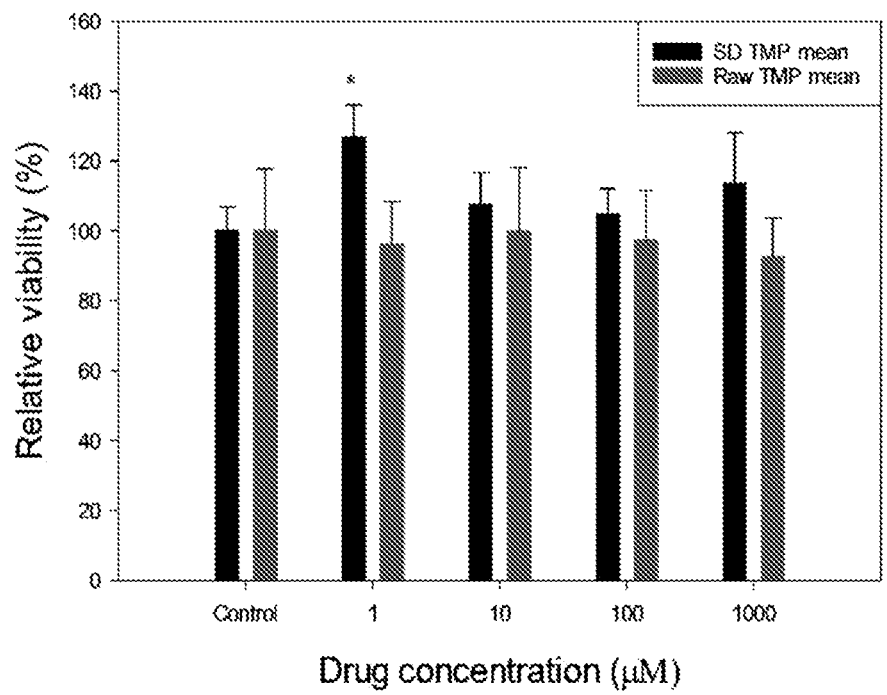
FIG. 8: Cell Viability of A) A549; and B) H358 Pulmonary Cell Lines. *pvalue<0.001, pvalue 0.010, *pvalue 0.015
Figure 8:
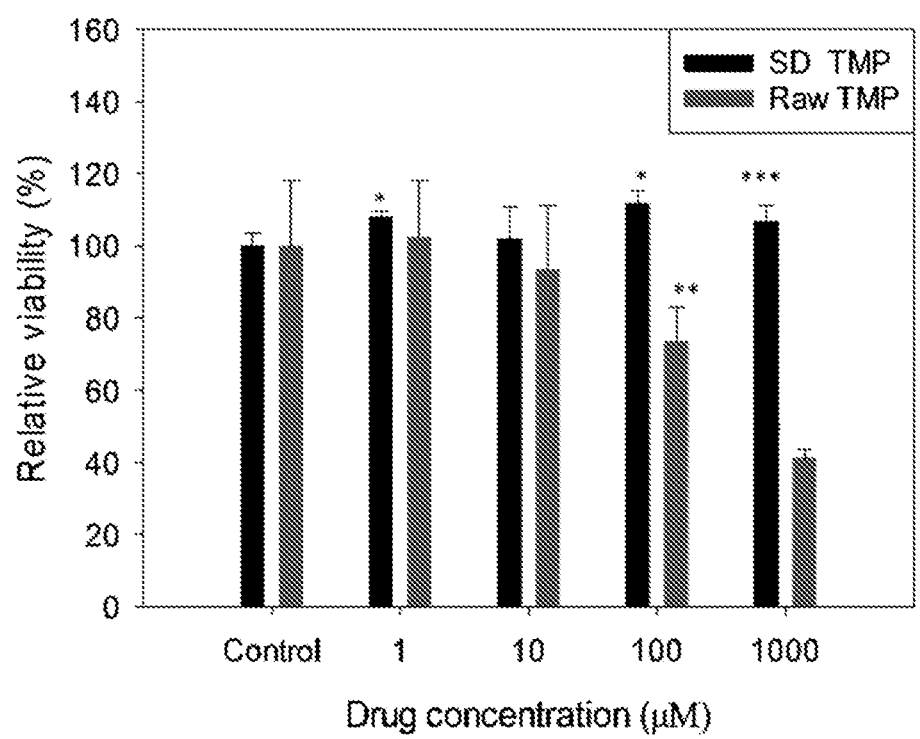

In vitro cell viability assay were performed on human pulmonary cell lines A549 and H358 representing different regions of the lung. Molar concentrations of 1, 10, 100 and 1000 μM of raw and SD TMP were tested. The relative cell viability of A549 cell line was found to be almost 100% for both raw and SD TMP at all concentrations. The relative viability of H358 cell line was 100% for SD TMP, however, at higher concentration, the viability was decreased. The cell viability using different concentrations is shown in FIG. 8.

In Vitro Transepithelial Electrical Resistance Analysis

Figure 9:
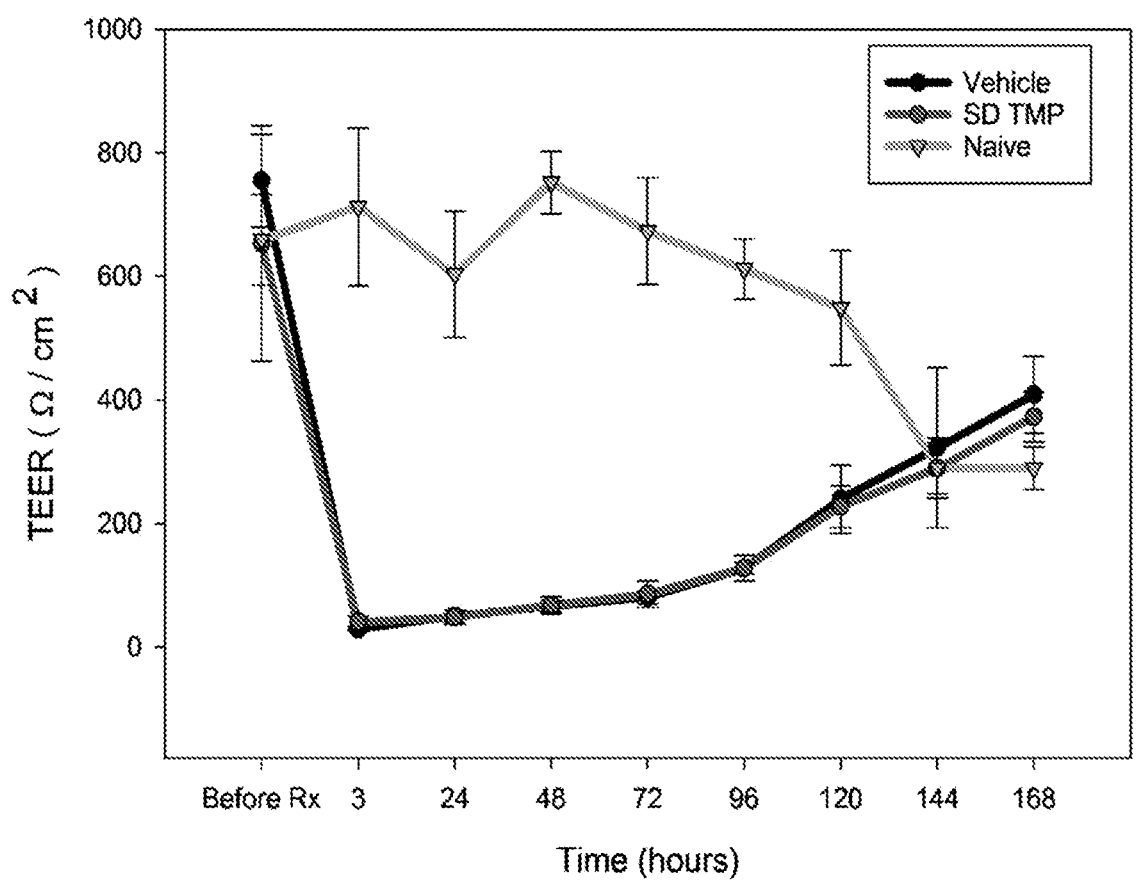
FIG. 9: Transepithelial Electrical Resistance (TEER) measurements using Calu-3 pulmonary cell lines.

It can be seen from the FIG. 9 that 3 hours after treatment of the cells with 100 μM of SD TMP using a microsprayer, the electrical resistance decreases drastically, however on continuous culturing for seven days following the treatment, the resistance was regained. Human Calu-3 pulmonary cells treated with the vehicle (10% ethanol+90% EMEM non-supplemented media) had a similar trend of decreased resistance three hours after treatment, followed by gradual increase in the resistance over a period of time.

In Vivo Efficacy Studies

Figure 10A:
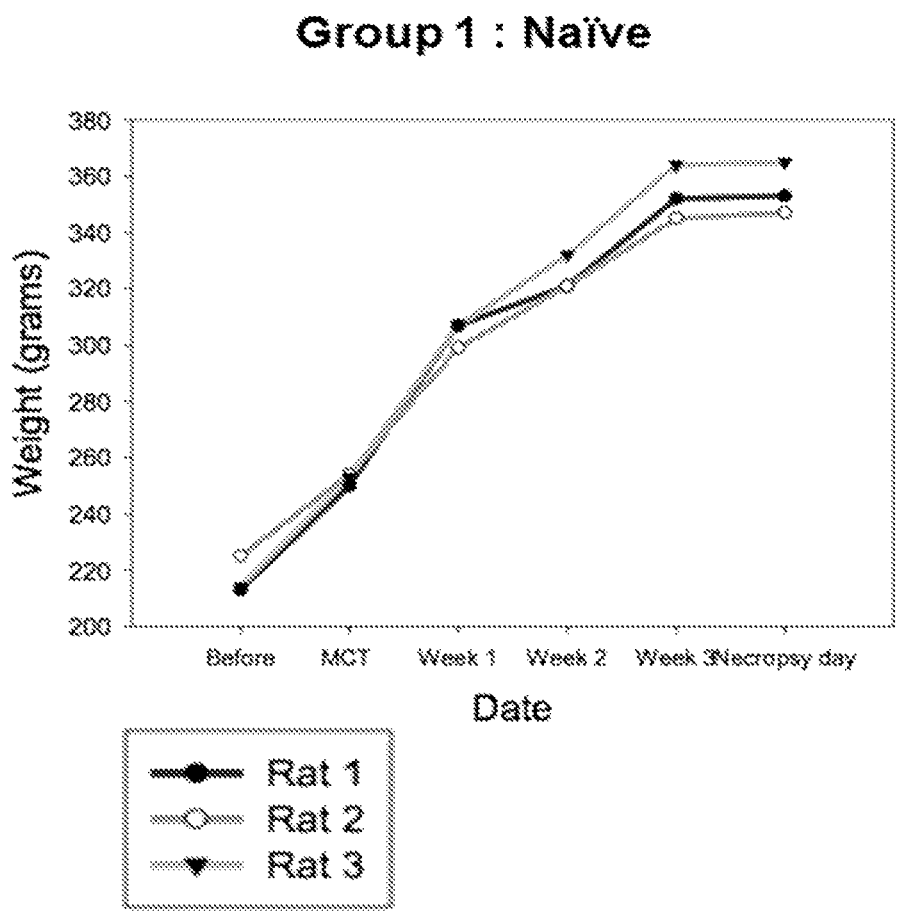
FIG. 10A-C: Rat Body Weights of Rats Measured Weekly.
Figure 10B:
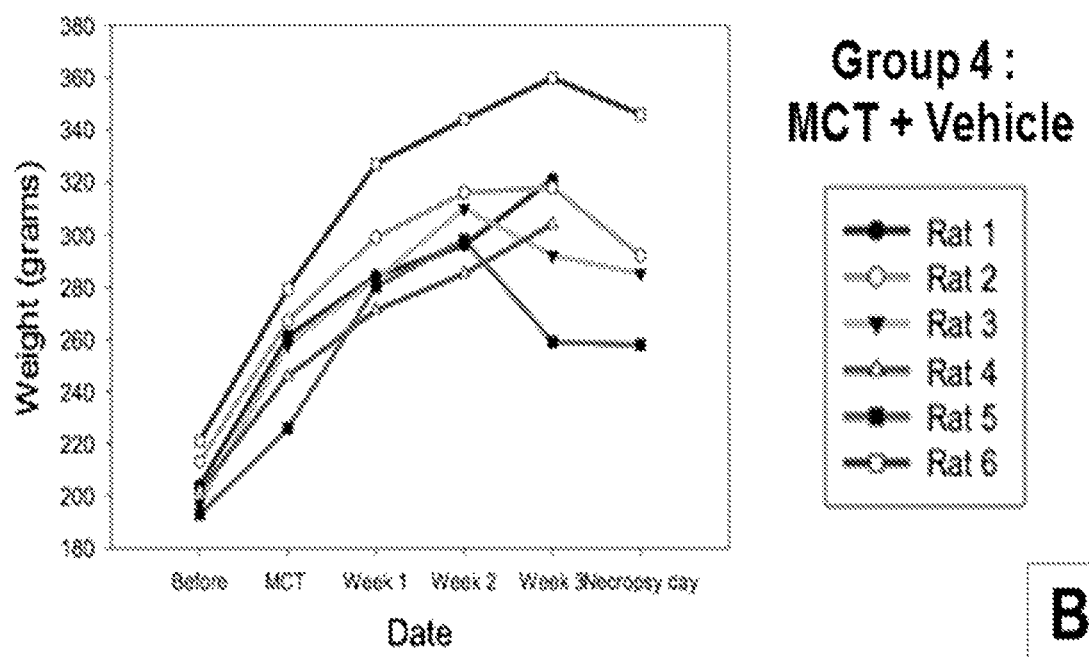
Figure 10C:
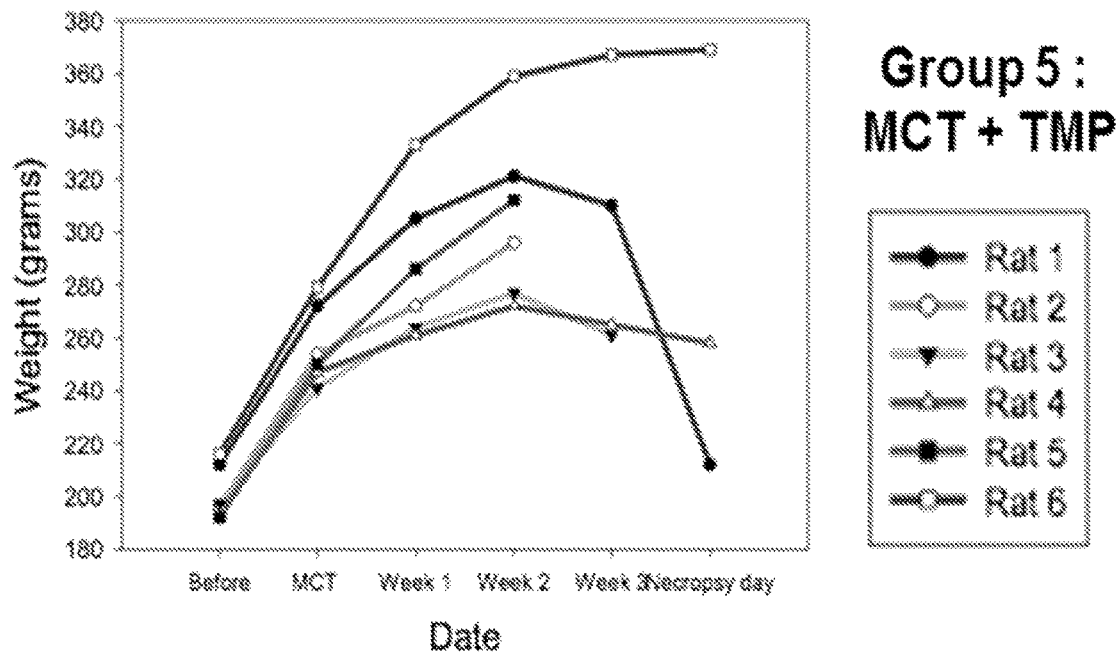
Figure 11:
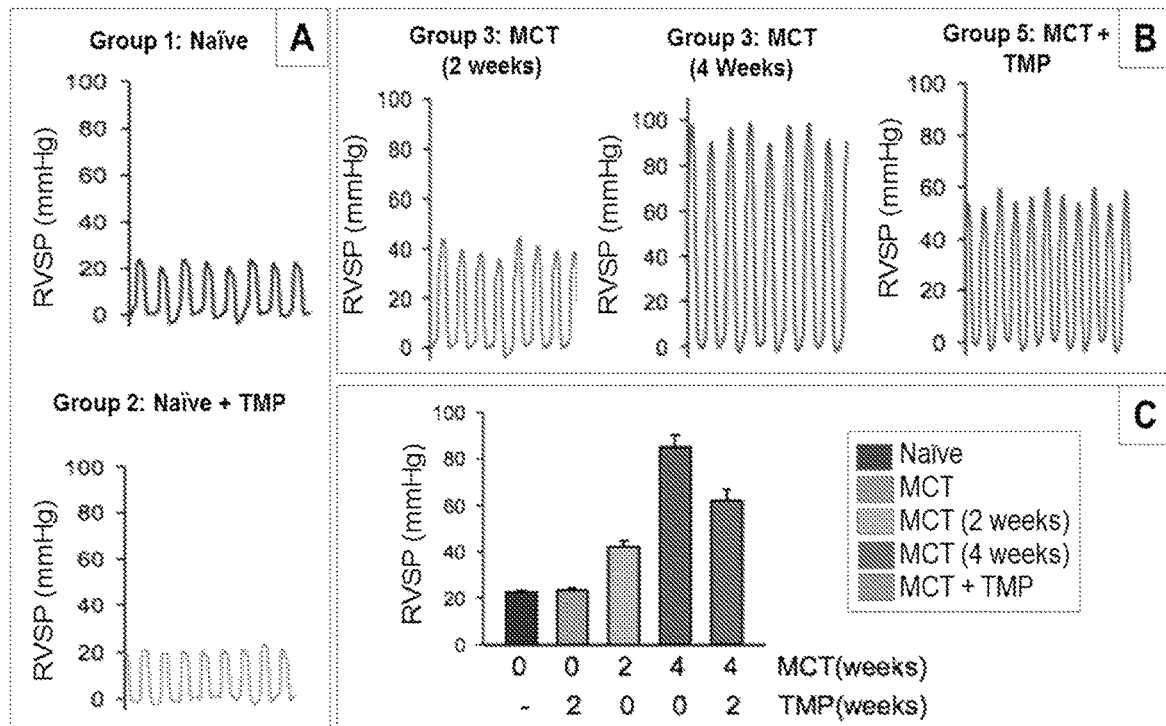
FIG. 11A-C: In Vivo Right Ventricle Systolic Pressure (RVSP) Measurements.

The rats body weight plots in FIG. 10 clearly show a significant loss of weight with time for the groups 4 and 5 that received MCT. In contrast the group 1 (Naive) rats showed a steady increase in body weight with time (FIG. 10). As it is presented in FIG. 11 and Table 3, the RVSP measurements in groups 1 (Naïve) and 2 (Naïve+TMP) are ranging between 20-25 mmHg (normal RV pressure in rats). Two weeks after MCT administration, the RVSP considerably increased to ~40-50 mmHg, as can be seen in FIG. 11B. Four weeks after MCT administration, the RVSP increased even more to ~80-100 mmHg in the untreated group 3. It is evident from the FIG. 11 B that after two weeks of aerosol treatment with SD TMP (group 5) the RVSP significantly decreased by ~20-30 units of mmHg relative to group 3 (4 weeks). It is worth mentioning that the insufflator device used to administer the powder had no effect on the RVSP of group 4 rats.

This is the first time tetramethylpyrazine has been developed and formulated as dry powder aerosol using advanced organic closed mode spray drying process. The spray dried particles were comprehensively characterized to test its suitability for pulmonary drug delivery. From the results obtained in the cellular studies, it is can be noted that the spray dried TMP formulation is safe for administration to the lower respiratory tract. However, the spray drying process has changed the physical property of the drug by causing a polymorphic conversion of the raw (unprocessed) compound. This is evident from the missing peaks in the XRPD diffractogram between 2θ values of 30-50°. Previously Zhang et al reported the X-ray diffraction pattern of Ligustrazine that is similar to the raw TMP diffraction pattern (Zhang X, et al., The Journal of pharmacy and pharmacology. February 2015; 67(2):160-169). When the drug was formulated with a PLGA carrier, the crystallinity changed with the difference in its miscibility with PLGA. Spray drying generally causes disruption to the crystallinity of a compound rendering it amorphous. The particle sizing using laser diffraction shows the size range of SD TMP particles to be between 4-14 μm, which is relatively larger to reach the vasculature in the lower respiratory track. The microscopic appearance of TMP in SEM micrographs indicates that the particles don't form spherical particles; it is also possible that the particles aggregate to different extends to form different sized aggregate/agglomerates.

The feasibility of using TMP as a pulmonary drug delivery was tested at the different molar concentrations of raw and SD formulations that show that SD TMP didn't affect the cell viability of both A549 and H358 pulmonary cell lines. The observed decrease in H358 viability in raw TMP could be due to the different polymorph. This means that up to 7 mg of the spray dried drug was found not to be toxic to pulmonary cell lines that were tested. Local delivery to the lungs requires less mass of the drug, generally in the range of few micrograms. Hence, the safety of this drug is high.

The in vivo data showed that the MCT model successfully achieved PH in the rodent after two weeks of administration via intraperitoneal route. The RVSP significantly increased after four weeks of MCT administration as reported previously. The body weight plots are in good agreement with the development of the disease as it can be seen in FIG. 10, where group 3 (MCT) rats lost weight with time. In contrast, group 1 (naïve) rats gained weight with time and maintained after certain point as it was expected. Regarding the RVSP, it was noticed that groups 1 and 2 rats with and without drug (TMP) treatment maintained a pressure of ~25 mmHg, which is normal in naïve rats. After two weeks of the MCT injection one can see an increase in the RVSP pressure but it was after four weeks that the increase in the RVSP reveals severe PH. It was noticed that the treatment of the rats with SD TMP (group 5) for 2 weeks has a noticeable impact in the decrease of RVSP pressure. Therefore, the results from this study show that TMP when administered as dry powder aerosol, has the ability to prevent the progression of PH in the MCT induced PH rat model.

TABLE 1

Physical properties of raw TMP and spray dried TMP

| Property Measured | Raw TMP | SD TMP |
|---|---|---|
| Particle sizing $D_{v10}$ | — | 4.186 ± 0.701 μm |
| Particle sizing $D_{v50}$ | — | 6.156 ± 1.147 μm |
| Particle sizing $D_{v90}$ | — | 14.552 ± 4.928 μm |
| Particle sizing span value | — | 1.684 ± 0.645 |
| DSC Endotherm (peak | 85.93 ± 0.71° C. | 85.11 ± 0.36° C. |
| DSC Endotherm Enthalpy | 152.5 ± 5.27 J/g | 149.2 ± 7.91 J/g |
| Residual water content | 0.633 ± 0.251% w/w | 0.368 ± 0.103% w/w |

TABLE 2

Aerosol dispersion performance of spray dried TMP particles using Aerolizer ®, Neohaler ® and Handihaler ®

| Inhaler device | Emitted dose (mg) Emitted Fraction (%) | Fine Particle Dose (mg) Fine Particle Fraction (%) | Respirable Dose (mg) Respirable Fraction (%) | MMAD (μm) | GSD |
|---|---|---|---|---|---|
| Handihaler | 86.92 100 ± 2.03 | 3.33 3.83 ± 0.42 | 37.24 8.9 ± 3.87 | 68.4 ± 49.63 | 5.28 |
| Neohaler | 79.28 88.41 ± 6.70 | 3.48 4.36 ± 0.65 | 25.19 14.87 ± 7.30 | 43.73 ± 38.67 | 42.40 |
| Aerolizer | 79.98 88.76 ± 7.27 | 1.15 1.41 ± 0.57 | 8.16 14.86 ± 8.0 | 15.23 ± 12.44 | 2.88 |

TABLE 3

In Vivo Right Ventricle Systolic Pressure (RVSP) Measurements made in rats

| Group 1(Naïve) | Group 2(Naïve + TMP) | Group 3 (MCT for 2 weeks) | Group 3 (MCT for 4 weeks) | Group 5 (MCT + TMP) |
|---|---|---|---|---|
| 22.5330 | 20.8110 | 39.4080 | 97.6720 | 78.2010 |
| 21.9020 | 24.2410 | 52.0390 | 95.7920 | 70.5310 |
| 20.9950 | 23.8990 | 38.4880 | 90.0360 | 58.6830 |
| 19.3520 | 24.7030 | 41.0640 | 95.1610 | 62.4200 |
| 22.3220 | 26.0550 | 40.3810 | 79.8910 | 43.3890 |
| 23.6890 | 19.6940 | | 78.3780 | 59.8200 |

Example 2

Materials and Methods
Materials

Figure 12:
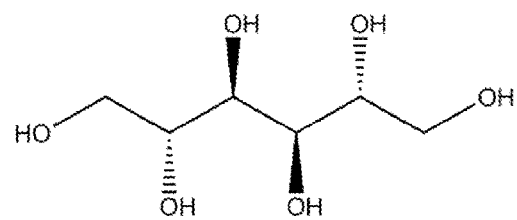
FIG. 12: Chemical Structure of D-Mannitol.
Figure 13:
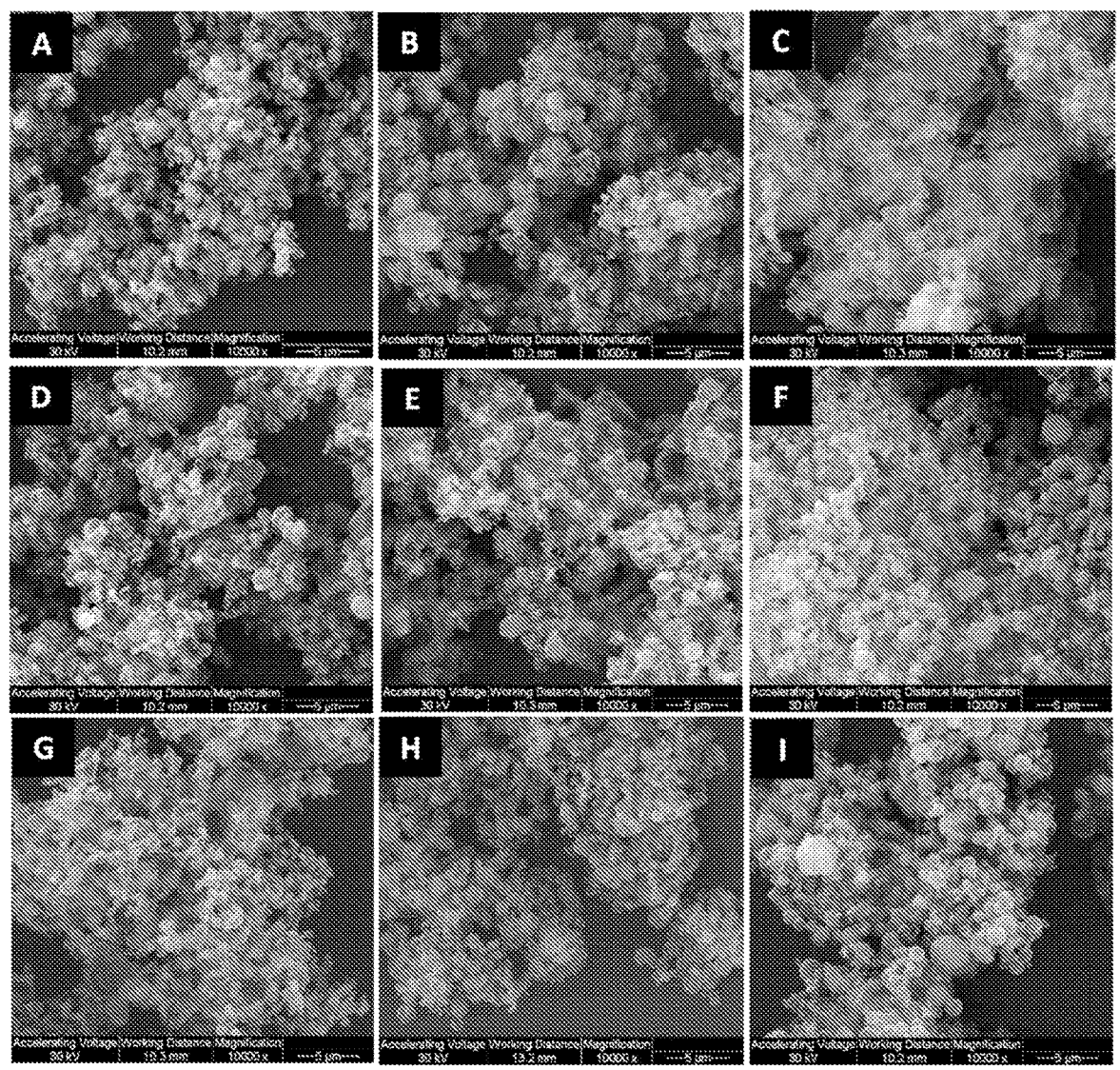
FIG. 13: SEM micrographs of co-spay dried (co-SD) tetramethylpyrazine: D-mannitol (TMP: Man) particles. (A) TMP: Man 75:25 (med P). (B) TMP: Man 75:25 (med-high P). (C) TMP: Man 75:25 (high P). (D) TMP: Man 50:50 (med P). (E) TMP: Man 50:50 (med-high P). (F) TMP: Man 50:50 (high P). (G) TMP: Man 25:75 (med P). (H) TMP: Man 25:75 (med-high P). (I) TMP: Man 25:75 (high P).
Figure 14:
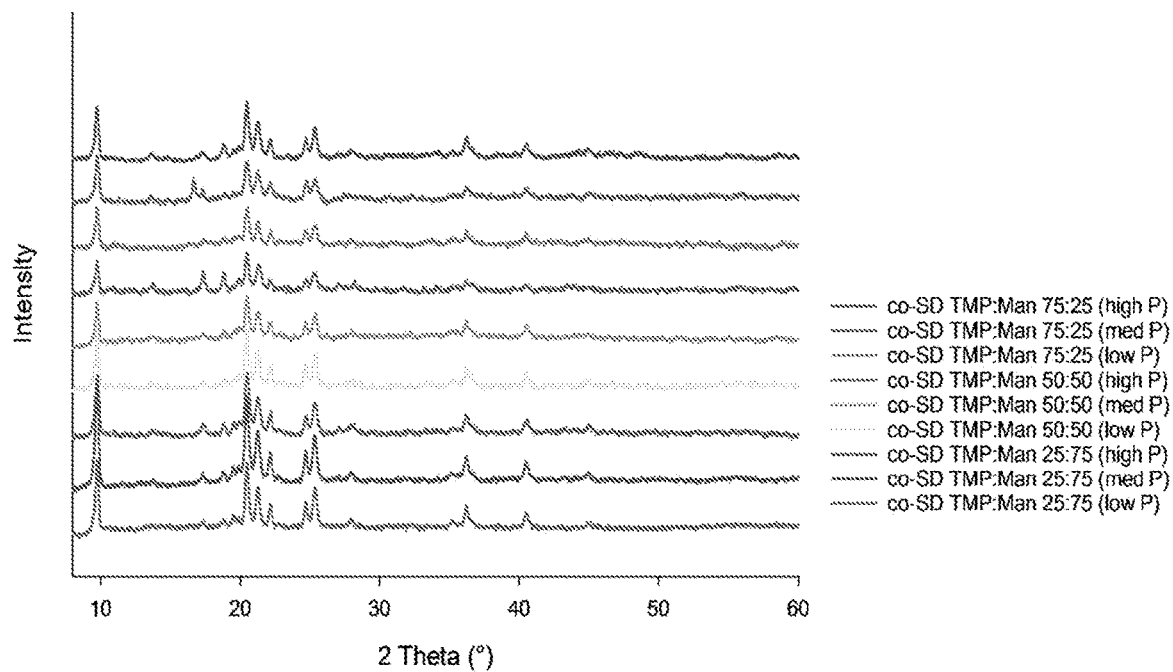
FIG. 14: X-ray powder diffractograms of co-spray dried tetramethylpyrazine:D-mannitol (co-SD TMP:Man) powders.
Figure 15:
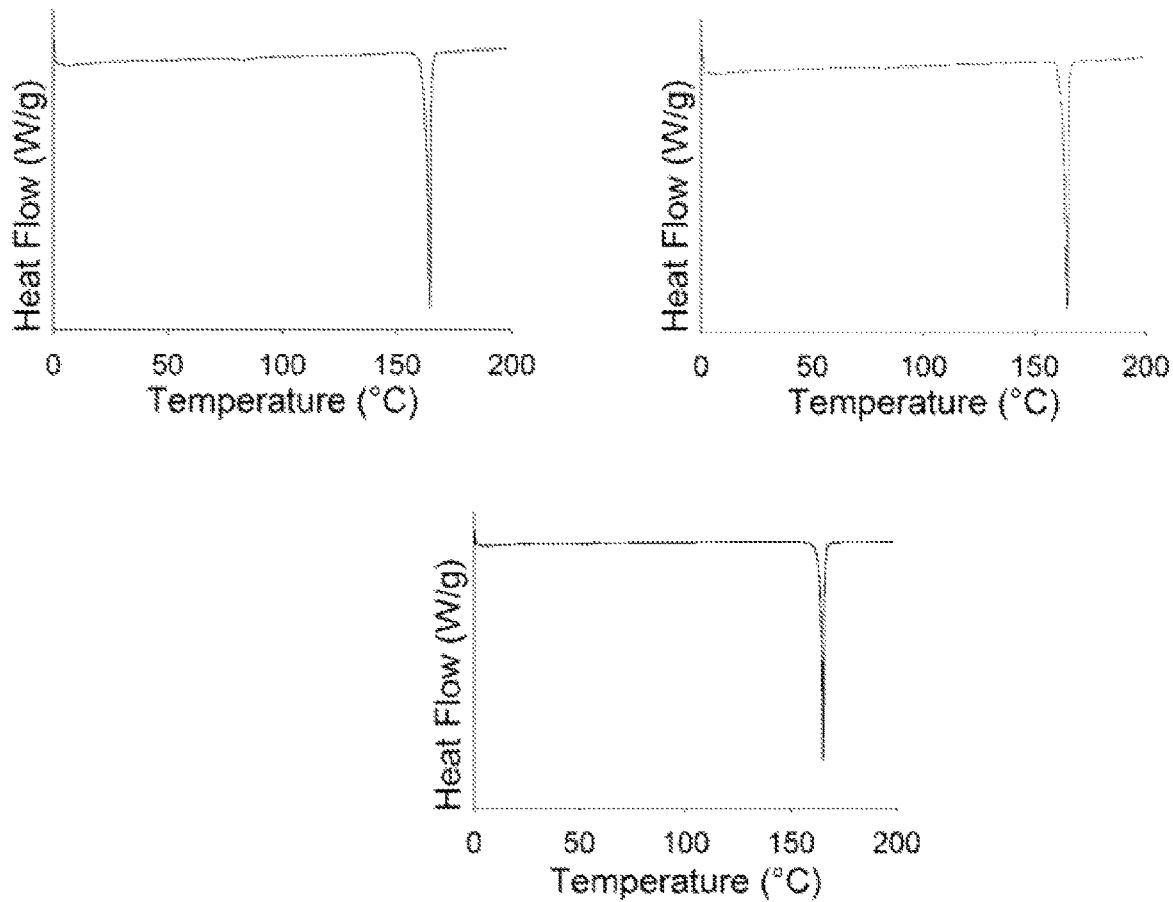
FIG. 15: Representative DSC thermographs of A) co-SD TMP: Man 75:25; B) co-SD TMP: Man 50:50; and C) co-SD TMP: Man 25:75.
Figure 16:
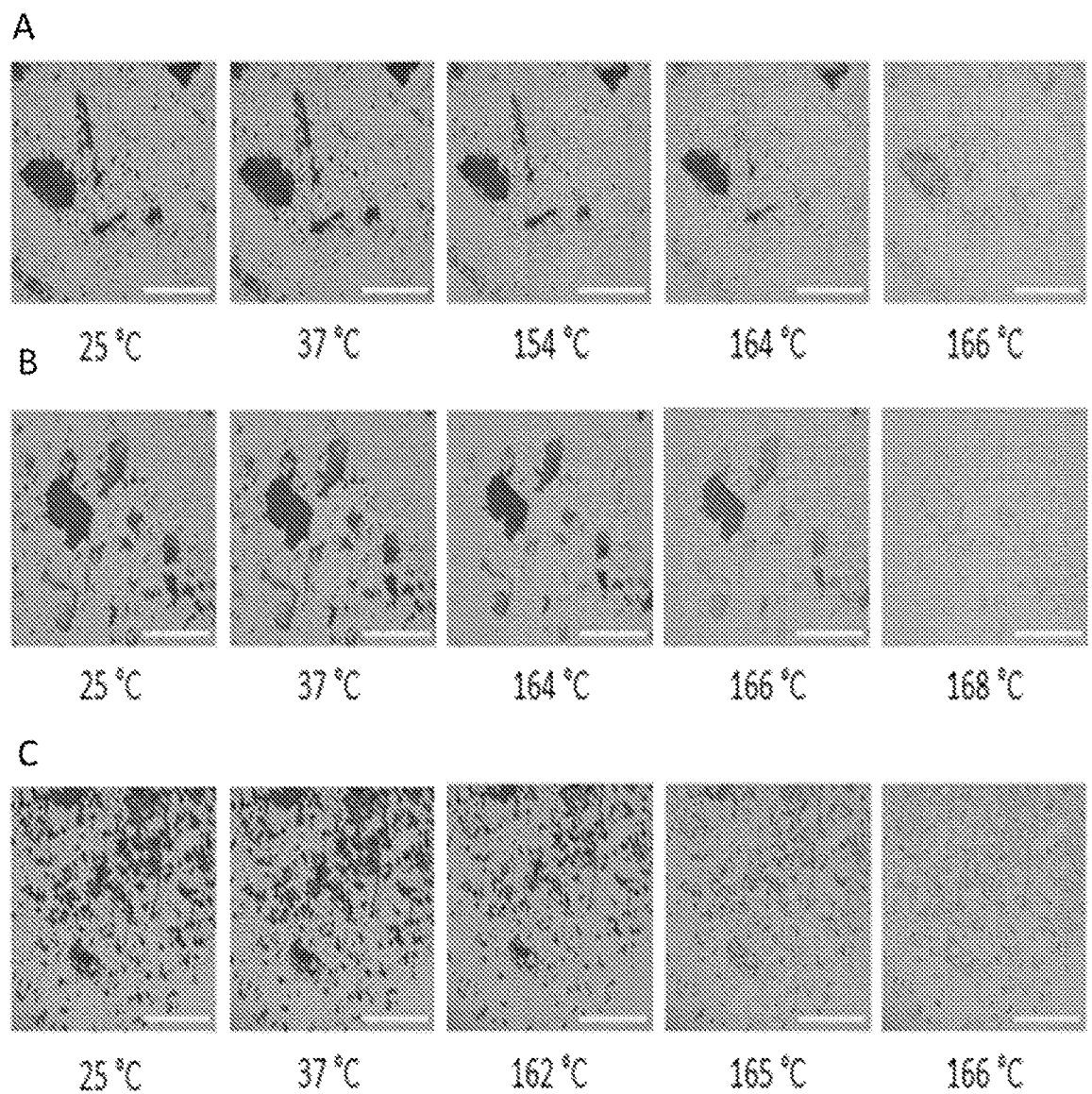
FIG. 16: Representative hot-stage microscopy (HSM) images at different temperatures of A) co-SD TMP: Man 75:25; B) co-SD TMP: Man 50:50; C) co-SD TMP: Man 25:75. Scale bar is 3 mm in length.
Figure 17:
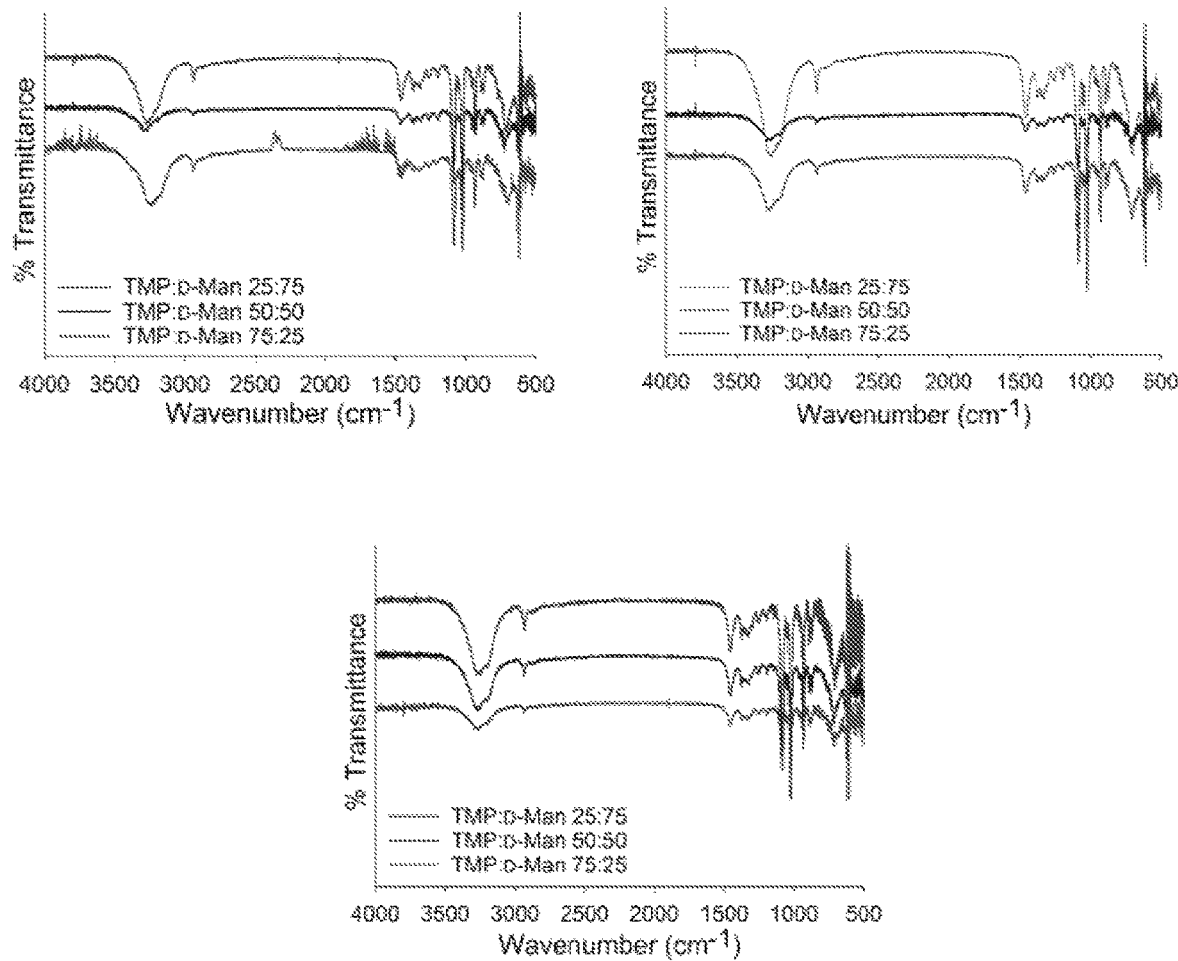
FIG. 17: Attenuated total reflectance-Fourier transform infrared (ATR-FTIR) spectra for: A) co-SD TMP:Man powders designed at med spray drying pump rate; B) co-SD TMP: Man powders designed at med-high spray drying pump rate; C) co-SD TMP: Man powders designed at high spray drying pump rate.
Figure 18A:
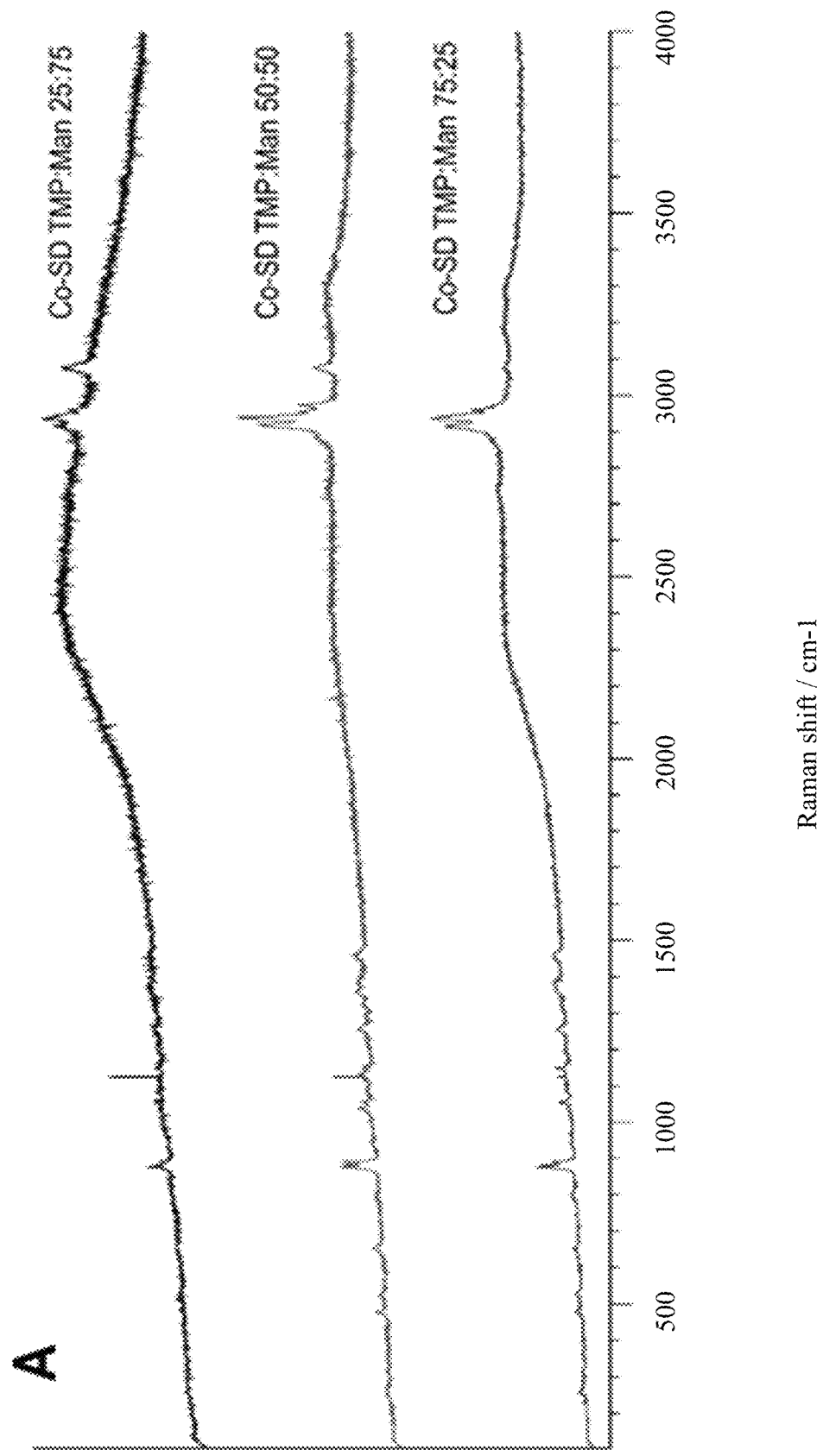
FIG. 18: Raman Spectra of A) co-SD TMP: Man powders designed at high spray drying pump rate; B) co-SD TMP: Man powders designed at med-high spray drying pump rate; C) co-SD TMP: Man powders designed at med spray drying pump rate.
Figure 18B:
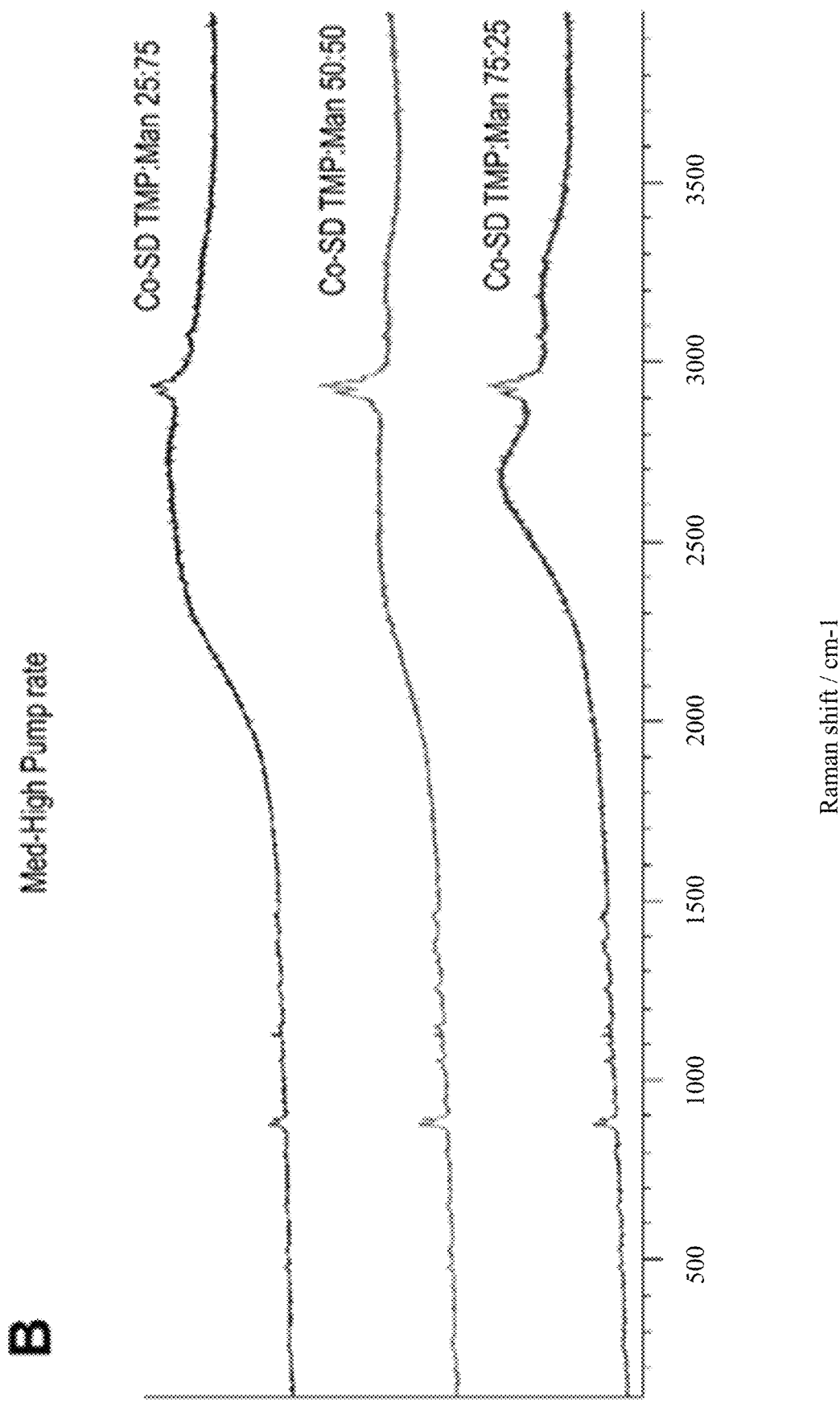
Figure 18C:
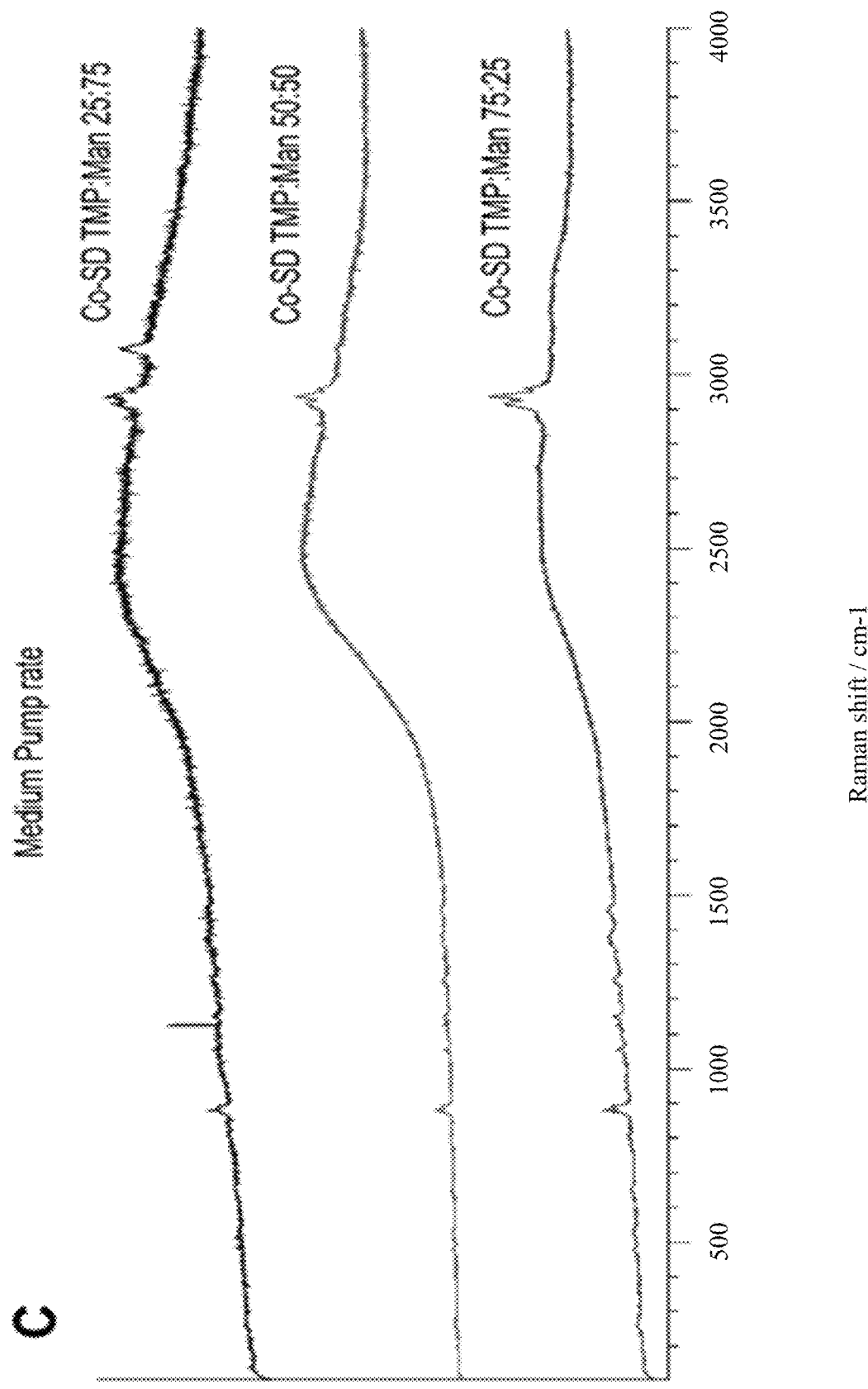
Figure 19:
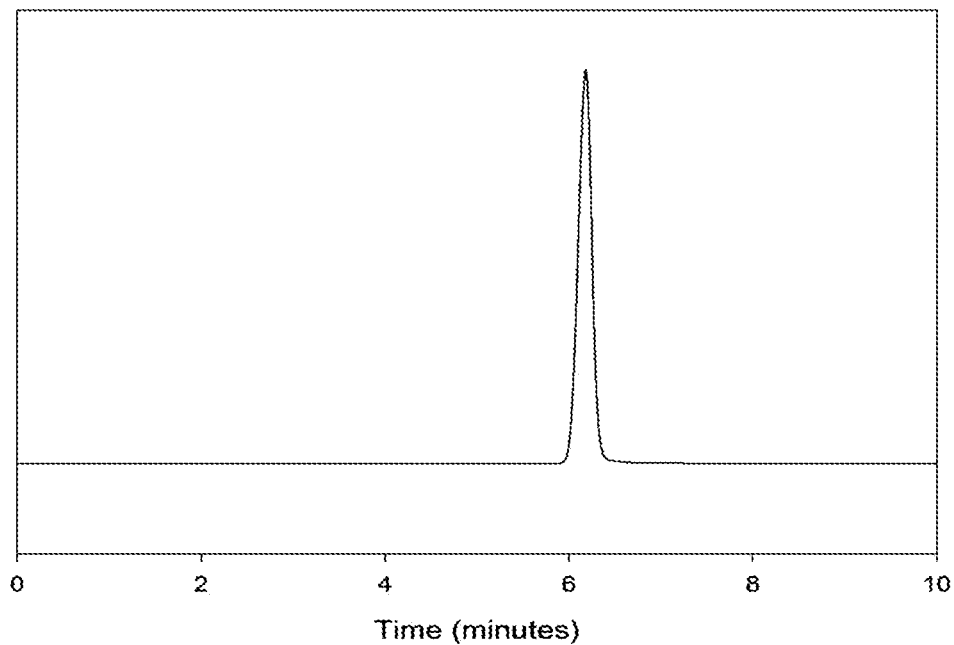
FIG. 19: HPLC chromatogram of TMP using UV-detector at 280 nm.

TMP [≥98% purity] [$C_8H_{12}N_2$; molecular weight (MW): 136.19] was obtained from Sigma-Aldrich (St. Louis, Mo.). Raw D-Man ($C_6H_{14}O_6$; MW: 182.17 g mol-1) (FIG. 12) was obtained from ACROS Organics (New Jersey, USA). Methanol (HPLC grade, ACS-certified grade, purity 99.9%) was obtained from Fisher Scientific (Fair Lawn, N.J.). HYDRANAL®-Coulomat AD was from Sigma-Aldrich. Resazurin sodium salt was obtained from ACROS Organics. DMSO LC-MS grade was from Thermo Scientific. The nitrogen gas used was ultra-high purity (UHP) (Cryogenics and gas facility, The University of Arizona, Tucson, Ariz.).

Human pulmonary cell lines were purchased from the American Type Culture Collection ATCC® A549 (ATCC® CCL-185™) and H358 (ATCC® CRL-5807™) Dulbecco's modified Eagle's medium (DMEM), Advanced 1X, Fetal Bovine Serum (FBS), Pen-Strep, Fungizone®, and L-Glutamine were obtained from Gibco® by Life Technologies (Thermo Fisher Scientific Inc, USA).

Advanced Closed Mode Spray Drying from Organic Solution

Spray drying was carried out using a B-290 Buchi Mini Spray Dryer coupled with a B-295 Inert Loop and high-performance cyclone (Buchi Labortechnik AG, Switzerland) in closed mode using compressed UHP dry nitrogen as the atomizing gas. The feed solutions were prepared by dissolving the components in methanol consisting of D-Man and TMP at rationally selected molar ratios. Table 4 lists the spray drying conditions that were utilized during the process for each different formulation. The stainless steel nozzle diameter was 0.7 mm. All co-spray dried (co-SD) particles were separated from the drying gas via dry nitrogen in the high-performance cyclone and collected in a small glass sample collector. The following SD conditions were used: atomization gas flow rate 6701 h$^{-1}$ (55 mm), aspiration rate of 38 m$^3$ h$^{-1}$ (100%), inlet temperature of 80° C. The spray drying pump rates used were high, medium-high, and medium which correspond to 30 ml/min (100%), 22.5 ml/min (75%), and 15 ml/min (50%), respectively. All co-SD powders were stored in desiccant conditions at −20° C. until further analysis.

TABLE 4

Advanced spray-drying conditions for co-spray dried (co-SD) TMP:Man powders.

| Powder composition | Molar ratio (TMP:$_D$-Man) | Feed concentration (% w/v) | Pump rate (%) | Inlet T (° C.) | Outlet T (° C.) |
|---|---|---|---|---|---|
| Co-SD TMP:Man | 75:25 | 0.4 | High (100%) | 80 | 10-13 |
| Co-SD TMP:Man | 75:25 | 0.4 | Med-high (75%) | 80 | 13-14 |
| Co-SD TMP:Man | 75:25 | 0.4 | Med (50%) | 80 | 24 |
| Co-SD TMP:Man | 50:50 | 0.18 | High (100%) | 80 | 9-12 |
| Co-SD TMP:Man | 50:50 | 0.18 | Med-high (75%) | 80 | 15-18 |
| Co-SD TMP:Man | 50:50 | 0.18 | Med (50%) | 80 | 14-17 |
| Co-SD TMP:Man | 25:75 | 0.1 | High (100%) | 80 | 7-9 |
| Co-SD TMP:Man | 25:75 | 0.1 | Med-high (75%) | 80 | 14-16 |
| Co-SD TMP:Man | 25:75 | 0.1 | Med (50%) | 80 | 25-27 |

Scanning Electron Microscopy

Using previously described conditions (Meenach et al., 2014, supra; Muralidharan et al., 2016; supra) the shape and surface morphology of particles were evaluated by scanning electron microscopy (SEM), using a SEM FEI Inspect S (Brno, Czeck Republic). Samples were placed on a double coated carbon conductive adhesive Pelco tabs' (TedPella Inc., Redding, Calif., USA), which were adhered to aluminum stubs (TedPella Inc., Redding, Calif., USA). Samples were coated with a gold thin film using a Hummer 6.2 sputtering system from Anatech (Union City, Calif.). The coating process was operated at 15 AC milliAmperes with about 7 kV of voltage for 3 minutes. The electron beam with an accelerating voltage of 30 kV was used at a working distance of 9-12.5 mm. Several magnification levels were used.

Particle Sizing and Size Distribution Using SEM Micrographs

The mean size, standard deviation and size range of the particles were determined digitally using SigmaScan Pro 5.0.0 (Systat, San Jose, Calif., USA), using similar conditions previously reported (Muralidharan et al., 2016; supra). Representative micrographs for each sample at 10,000× magnification were analyzed by measuring the diameter of at least 100 particles per sample. In addition, number weighted size distributions were defined to calculate $D_{n10}$, $D_{n50}$, and $D_{n90}$ parameters. The span value was calculated using the equation 7 defined as:

$$\text{Span} = \frac{Dn90 - Dn10}{Dn50} \quad \text{Equation 7}$$

X-Ray Powder Diffraction (XRPD)

Using similar conditions to those described (Meenach et al., 2014, supra; Muralidharan et al., 2016; supra), X-ray powder diffraction (XRPD) patterns of samples were collected at room temperature with a PanAnalytical X'pert diffractometer (PANalytical Inc., Westborough, Mass., USA) with Cu Kα radiation (45 kV, 40 mA, and λ=1.5406 Å) between 5.0 and 65.0 (2θ) with a scan rate of 2.00° per minute at ambient temperature. The powder samples were loaded on zero background silicon wafer sample holder and diffraction was measured with an X'celerator detector.

Differential Scanning Calorimetry (DSC)

Thermal analysis and phase transitions measurements were performed using a TA Q1000 differential scanning calorimeter (DSC) (TA Instruments, New Castle, Del.) equipped with T-Zero® technology, and RSC90 automated cooling system. Approximately a mass of 1-3 mg of powder was weighted into a hermetic anodized aluminum T-Zero® DSC pan. These were hermetically sealed with a T-Zero hermetic press (TA Instruments). An empty hermetically sealed pan was used as reference pan. UHP nitrogen gas was used at a rate of 40 mL min$^{-1}$. All samples were heated starting at 0° C. to 200° C. at a scanning rate of 5.00° C. min$^{-1}$. All measurements were done in triplicate (n=3).

Hot-Stage Microscopy (HSM) Under Cross-Polarizers

Using similar conditions reported by previous authors (Meenach et al., 2014, supra; Muralidharan et al., 2016; supra), hot-stage microscopy (HSM) was performed using a Leica DMLP cross-polarized microscope (Wetzlar, Germany) equipped with a Mettler FP 80 central processor heating unit and Mettler FP82 hot stage (Columbus, Ohio, USA). Samples were mounted on cover glass slide and heated from 25.0° C. to 200.0° C. at a heating rate of 5.00° C. min$^{-1}$. The images were digitally captured using a Nikon coolpix 8800 digital camera (Nikon, Tokyo, Japan) under 10× optical objective and 10× digital zoom.

Karl Fisher Coulometric Titration

The residual water content of all SD and co-SD powders were analytically quantified by Karl Fischer (KF) coulometric titration, using a TritoLine® 7500 KF trace coupled with a TM 235 (SI Analytics GmbH, Mainz, Germany). Approximately 1-2 mg of powder were added directly into the reaction cell that contained Hydranal® AD reagent.

Confocal Raman Microspectroscopy (CRM) and Chemical Imaging

Microspectroscopic component analysis of DPI formulations was carried by the noninvasive and nondestructive Raman spectroscopy. Using similar conditions previously reported (Meenach et al., 2014, supra; Muralidharan et al., 2016; supra; Li X, et al., European Journal of Pharmaceutical Sciences. 2014; 52:191-205; Meenach et al., 2013, supra), Raman spectra was obtained at 514 nm laser excitation using Renishaw InVia Reflex (Gloucestershire, UK) at the surface using a 20× magnification objective on a Leica DM2700 optical microscope (Wetzlar, Germany) and equipped with a Renishaw inVia Raman system (Gloucestershire, UK). This Renishaw system has a 24001/mm grating, with a slit width of 65 μm and a thermoelectrically cooled Master Renishaw CCD detector. The laser power was adjusted to achieve 5000 counts per second for the 520 cm-1 line of the internal Si Reference. Raman spectra was achieved using varying laser power (10-100%), and 10 seconds of exposure time on all samples.

Attenuated Total Reflectance-Fourier-Transform Infrared Spectroscopy (ATR-FTIR)

Attenuated total reflectance-Fourier-transform infrared spectroscopy (ATR-FTIR) was performed using a Nicolet Avatar 360 FTIR spectrometer (Varian Inc., CA) equipped with a DTGS attenuated total reflectance accessory. All the experiments were performed using similar conditions reported by the authors (Meenach et al., 2014, supra; Muralidharan et al., 2016). The powder was placed on a diamond ATR silicon crystal and held in place with a specialized clamp. Each spectrum was collected for 32 scans at a spectral resolution of 8 cm$^{-1}$ over the wavenumber range of 4000-400 cm$^{-1}$. The data were collected and analyzed using the EZ-OMNIC software.

Tetramethylpyrazine Drug Content Analysis by High Performance Liquid Chromatography (HPLC)

High-performance liquid chromatography (HPLC) was used to quantify the amount of TMP content in the co-SD formulated powders. This method was performed with similar conditions reported previously (Tsai T-H, Liang C-C. Int J Pharm. 2001; 216(1):61-66). This was performed with a LC-2010AHT HPLC system, with autosampler fitted to a 20 µl sampling loop and UV-Vis detector. Integration of the peaks was performed with the LabSolutions Postrun Analysis software. Compounds were separated on a 250×4.6 mm, 5 µm particle size (Altima C18 5µ, GRACE, Illinois, USA) Cis reverse-phase column. The mobile phase consisted of methanol-water (50:50, v/v, pH 3.0 adjusted by orthophosphoric acid) delivered at a flow rate of 1.0 ml min$^{-1}$. TMP was monitored at a wavelength of 280 nm through the experiments. The total chromatographic run time was 10 min. Under these conditions, the relative retention time of TMP was approximately 5.9 min. all calibration curves were required to have a correlation value at least 0.995. Calibration standard solutions were diluted in methanol at 0.001, 0.01, 0.1, 0.25, 0.5, 1 mg/ml. All calibration standards and unknowns were analyzed in triplicate (n=3). The TMP loading content was calculated as follow with equation 8:

$$\text{Drug loading} = \frac{\text{Actual mass of } TMP}{\text{Mass of particles}} \quad \text{Equation 8}$$

In Vitro Aerosol Dispersion Performance

In accordance with US Pharmacopeia (USP) Chapter <601> specification on aerosols and using conditions similar to previously reported, the in vitro aerosol dispersion properties of the dry powder particles were determined using the Next Generation Impactor® (NGI®) with a stainless steel induction port (USP throat) attachment (NGI® Model 170), equipped with specialized stainless steel NGI® gravimetric insert cups (MSP Corporation, Shoreview, Md., USA). The NGI® was coupled with a Copley TPK 2000 critical flow controller connected to a Copley HCP5 vacuum pump, and the airflow rate (Q), was measured and adjusted prior to each experiment using a Copley DFM 200 flow meter (Copley Scientific, UK).

The mass of powder deposited on each stage was quantified by gravimetric method using type A/E glass fiber filters with diameter 55 mm (PALL Corporation, Port Washington, N.Y.) and 75 mm (Advance, Japan). Quali-V clear HPMC size 3 inhalation grade capsules (Qualicaps, North Carolina) filled with about 10 mg of powder were used. Three capsules were used in each experiment. In vitro aerosolization was done in triplicate (n=3) under ambient conditions. The NGI™ was operated at a flow rate of 601 $min^{-1}$ with a delay time of 10 s before actuation of the inhaler, followed by 10 s of airflow through the inhaler. The glass fiber filter was measured gravimetrically before and after actuation, on each stage, to determine the particle stage deposition. The fine particle dose (FPD), fine particle fraction (FPF), respirable fraction (RF), and emitted dose (ED) were calculated using the 3-6 equations:

$$\text{Fine particle fraction } (FPF) = \frac{\text{Fine particle dose}}{\text{Initial particle mass loaded in capsules}} \times 100\% \qquad \text{Equation 10}$$

$$\text{Respirable fraction } (RF) = \frac{\text{Fine particle dose}}{\text{Total particle mass on all stages}} \times 100\% \qquad \text{Equation 11}$$

$$\text{Emitted dose } (ED) = \frac{\text{Initial mass in capsules} - \text{Final mass remaining in capsules}}{\text{Initial mass in capsules}} \times 100\% \qquad \text{Equation 12}$$

The mass mean aerodynamic diameter (MMAD) and geometric standard deviation (GSD) of aerosol dispersion profiles were determined using a Mathematica (Wolfram Research Inc., Champaign, Ill.) program written by Dr. Warren Finlay (Finlay W. The ARLA Respiratory Deposition Calculator. 2008).

In Vitro Cell Dose-Response Assay

Cell-based assays are often used to determine if test molecules have effects on cell proliferation or show direct cytotoxicity effects that eventually leads to cell death. The effects of TMP formulations were analyzed by measuring the response of lung adenocarcinoma cells at different concentrations of the drug. The A549 pulmonary cell line is a human alveolar epithelial lung adenocarcinoma cell line and has been used as a model of the alveolar type II pneumocyte cell in in vitro pulmonary drug delivery and metabolism studies. The H348 pulmonary cell line is a human bronchoalveolar epithelial cell line similar to alveolar type II cells and express lung surfactant associated protein A (SP-A) (Acosta M F, et al., Current pharmaceutical design. 2016; 22(17):2522-2531; Hickey A J, et al., DRUGS AND THE PHARMACEUTICAL SCIENCES. 2003; 126: 835-848). Both cell lines were grown in a growth medium including Dulbecco's modified Eagle's medium (DNEM) advanced 1×, 10% (v/v) fetal bovine serum (FBS), Pen-Strep (100 U $ml^{-1}$ penicillin, 100 μg $ml^{-1}$), Fungizone (0.5 μg $ml^{-1}$ amphotericin B, 0.41 μg $ml^{-1}$ sodium deoxycholate), and 2 mM L-Glutamine in a humidified incubator at 37° C. and 5% $CO_2$.

As previously reported (Hickey et al., supra), both cell lines were seeded in 96-well plates at 5000 cells/well and 100 μl/well and allowed to attach for 48 hours. Then, the cells were exposed to 100 μl of TMP dissolved in media at different concentrations and incubated for 72 hours after exposure. Continuously, 20 μl of 10 μM resazurin sodium salt dissolved to 1% DMSO in media was added to each well and incubated for 4 hours. At this point, the fluorescence intensity was detected at 544 nm (excitation) and 590 nm (emission) using a Synergy H1 Multi-Mode Reader (BioTek Instruments Inc., Winooski, Vt.). The relative viability of each sample was calculated as follow:

$$\text{Relative viability}(\%) = \frac{\text{Sample fluorescence intensity}}{\text{Control fluorescence intensity}} \times 100\% \qquad \text{Equation 13}$$

In Vitro Transepithelial Electrical Resistance Analysis Calu-3 lung epithelial cells, a human lung adenocarcinoma cell line derived from the bronchial submucosal airway region, were grown in a growth medium including Eagle's minimum essential medium (EMEM), 10% (v/v) fetal bovine serum (FBS), Pen-Strep (100 U ml-1 penicillin, 100 µg ml-1), Fungizone (0.5 µg ml-1 amphotericin B, 0.41 µg ml-1 sodium deoxycholate) in humidified incubator at 37° C. and 5% CO2, as previously reported Meenach et al., 2013, supra; Meenach et al., 2014, supra; Acosta et al., supra). The cells were seeded at 500,000 cells/ml in Costar Transwells® (0.4 µm polyester membrane, 12 mm for a 12-well plate) with 0.5 ml of media on the apical side and 1.5 ml of media on the basolateral side. Media was changed every other day from the basolateral and apical side. After 10 days of growth, when the cells reached a TEER value of about 1000 $\Omega/cm^2$ (indicator of a confluent monolayer at liquid covered culture (LCC)) the media was removed from both sides and 800 µl of media was added to the basolateral side of the Transwells to facilitate air-interface culture (AIC) conditions. The TEER responses of the cells were measured with an Endohom 12 mm Culture Cup (World Precision Instruments, Sarasota, Fla.). For TEER measurement, 0.5 ml of media was added to the apical side of the Transwell 5 min before measurement and then immediately removed to return the cells to AIC conditions. After the TEER values reached 500 $\Omega/cm^2$ (indicating a confluent monolayer at AIC conditions), the cells were exposed to 100 µM of SD TMP and representative co-SD formulations dissolved in non-supplemented EMEM media. The liquid aerosol formulations were delivered to the Calu-3 cells at AIC by using a Penn Century MicroSprayer® Aerolizer—Model IA-1B [1]. TEER values were then recorded for up to 7 days after aerosol treatment, as previously reported (Meenach et al., 2014, supra; Meenach et al., 2016, supra).

Statistical Analysis

All experiments were performed in at least triplicate (n=3) unless mentioned. All data was plotted and statistically analysis were run using Sigma Plot 13.0 (Systat Software Inc., San Jose, Calif.). Post analysis of in vitro aerosol performance, interaction of excipient and process parameter on the performance of the formulation was evaluated using the 3-D surface plot generated from Design Expert*8.0.7.1 software (Stat Ease Corporation, Minneapolis, Minn.). The results are expressed as mean standard deviation.

Results

Scanning Electron Microscopy (SEM)

The particle shape and surface morphology was visualized by SEM as shown in FIG. 13 for the co-SD TMP: Man systems. In general, co-SD particles made at medium spray drying pump rate (med P), exhibited smooth and spherical shape with slight sintering and agglomeration. Particles made at medium-high (med-high P) and high spray drying pump rate (high P) exhibited spherical and fairly crinkled surface morphology. It can also be observed that increasing TMP molar ratio concentration decreased the uniformity of the particles.

Particle Sizing and Size Distribution by Image Analysis of SEM Micrographs

The primary particle sizing and size distribution data of co-SD TMP: Man is summarized in Table 5. While all samples had a projected mean geometric diameter in the size range of 0.812-1.456 μm, there was a slight difference in the size distribution according to TMP content. However, only co-SD TMP: Man 25:75 med P showed significantly (P<0.001) smaller mean geometric diameter of 0.812 μm compared to all the other samples. The $D_{n50}$ values were in the range of ~0.741-1.264 μm. The $D_{n10}$ values were in the range of ~0.534-0.929 μm. The span values were between 0.726 μm and 1.671 μm. All co-SD particles had particle size range <5 μm, which is favored for inhalation powders (Muralidharan et al., 2016, supra).

X-Ray Powder Diffraction (XRPD)

The XRPD pattern of co-SD TMP: Man powders showed sharp peaks which are characteristics of long-range molecular order, as shown in FIG. 14. The peaks of co-SD powders resembled that of both TMP and Man. The molar ratio had no apparent effect on XRPD data for all co-SD TMP: Man powders.

Differential Scanning Calorimetry (DSC)

DSC thermograms of all co-SD TMP: Man particles are shown in FIG. 15. The co-SD TMP: Man particles showed a single sharp peak at ~165° C. independently of TMP molar ratio or spray drying pump rate. This may indicate molecular encapsulation of the drug in the excipient due to the presence of a single peak in a double component system (drug & excipient) (Muralidharan et al., 2016, supra). As can been seen in Table 6, there was an increase in heat of fusion of the co-SD systems indicating some level of molecular miscibility between the two components. There is also no phase transition at room temperature and body temperature seen in any of the samples.

Hot-Stage Microscopy under Cross-Polarizer Lens

FIG. 16 shows illustrative images for HSM experiment. All samples including co-SD samples exhibited birefringence which is consistent for crystalline powders. All co-SD TMP: Man samples exhibited only one observable transition from solid state to liquid state at higher temperatures of ~162-168° C. Same behavior was observed for high and medium pump rate co-SD samples (data not shown). There were no observable differences at room temperature (25° C.) and body temperature (37° C.) for any of the samples.

Karl Fisher Coulometric Titration (KFT)

The residual water content of the co-SD powders are listed in Table 7. For all the co-SD powders it can be noted that water content values were <1.75% w/w, which are considered acceptable for inhalable dry powder formulation.

Attenuated Total Reflectance-Fourier-Transform Infrared (ATR-FTIR) Spectroscopy

ATR-FTIR spectra of the formulated co-SD particles are shown in FIG. 17. In particular, strong peaks were present due to C—H stretching (2986 $cm^{-1}$), —$CH_3$ asymmetrical bending (1408 $cm^{-1}$), C—$H_3$ symmetrical bending (1358 $cm^{-1}$), C—N stretching (1223 $cm^{-1}$), —$CH_3$ rocking (988 $cm^{-1}$), and C—$CH_3$ stretching (800 $cm^{-1}$). With respect to the co-SD systems, all of them showed O—H stretching at 3260-3280 $cm^{-1}$, indicating the O—H bonding that is present in Man.

Confocal Raman Microspectroscopy (CRM) & Chemical Imaging

On confocal Raman microspectroscopy, as shown in FIG. 18, co-SD powders at all molar ratios and all pump rates showed peaks consistent with TMP and Man indicating the presence of both components. The sharp peaks in co-SD particles are indicative of crystallinity.

Tetramethylpyrazine Loading Analysis Via HPLC

FIG. 19 is a representative HPLC chromatogram showing the retention time of TMP at around 6 minutes. Table 8 shows TMP loading of the formulated co-SD particles analyzed via high-performance liquid chromatography. There was a spray drying pump rate effect, indicating that medium-high spray drying pump rate produced the highest drug loading irrespective of the molar ratio of the components. The co-SD TMP:Man 75:25 (med-high P) showed the highest TMP loading value of 0.1419 mg per milligram of powder.

In Vitro Aerosol Dispersion Performance via Next Generation Impactor™

Figure 20:
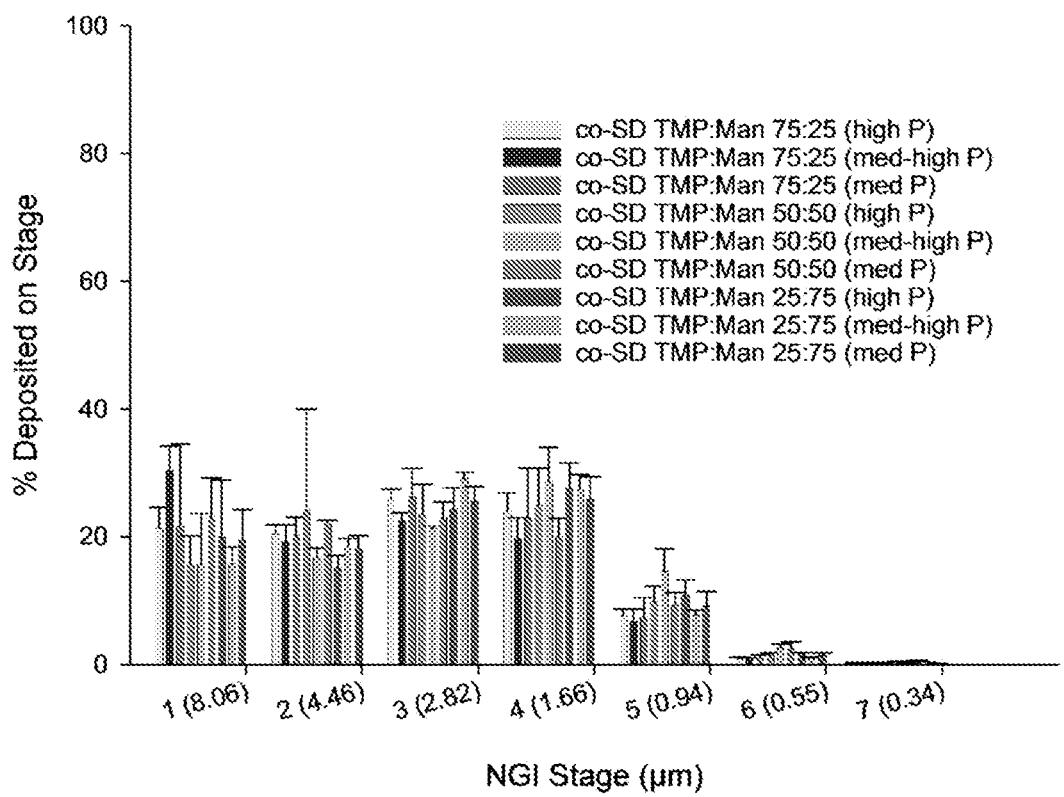
FIG. 20: Aerosol dispersion performance using the Next Generation Impactor® (NGI®) under an airflow Rate (Q) of 60 L/min with the HandiHaler® DPI device for co-spray dried tetramethylpyrazine:D-mannitol (co-SD TMP: Man) powders (n=3, mean SD).

The aerosol properties of all co-SD TMP: Man powders were assessed using an NGI® actuated with a Handihaler® human DPI device. As seen in Table 9, MMAD and GSD values decreased with the addition of Man for all the co-SD systems. The FPF and RF values also increased significantly with the addition of Man with FPF values ranging from 39.2% to 66.8% and RF values ranging from 69.5% to 84.3%. The ED values ranged from 89.6% to 98.4% for the co-SD systems but no significant difference was observed. FIG. 20 shows the actual aerosol dispersion performance of the formulated dry powder aerosols by presenting the percentage deposition of the particles on each of the NGI® stages. In particular, high deposition on the lower stages from stage 2 to stage 7 (which is desirable) was observed for formulated co-SD powders.

In Vitro Drug Dose-Response Analysis

Figure 21:
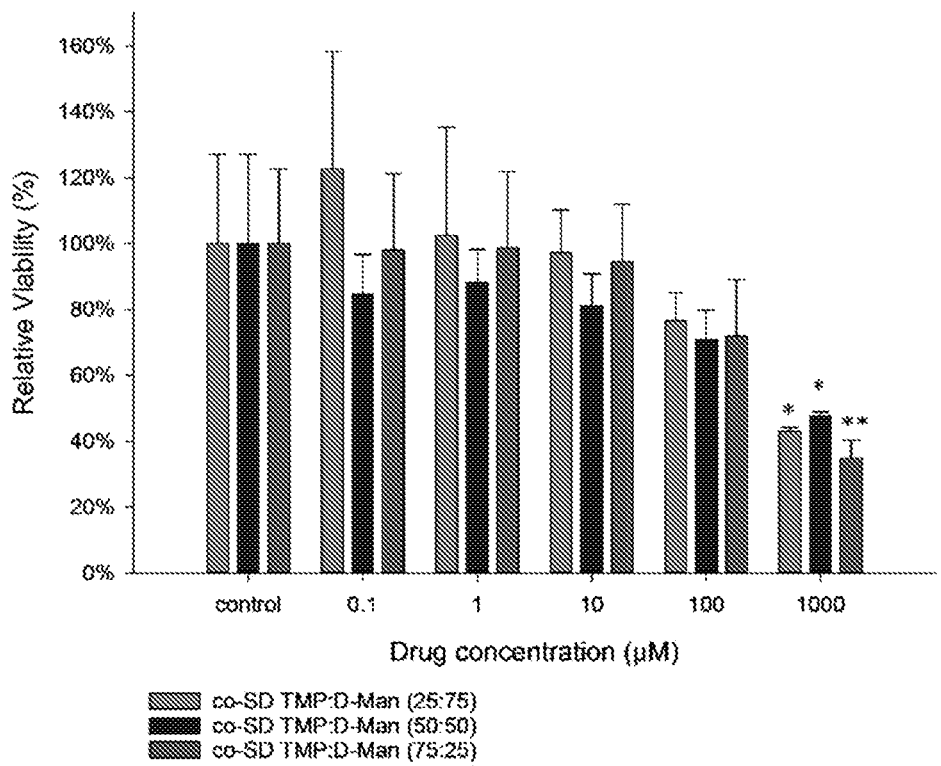
FIG. 21: In vitro drug dose-response for: (A) H358 cell dose-response to co-SD TMP: Man Powders; (B) A549 cell dose-response to co-SD TMP: Man Powders. *P<0.05 and **P<0.01 vs. control. (n=6, mean±SD)
Figure 21:
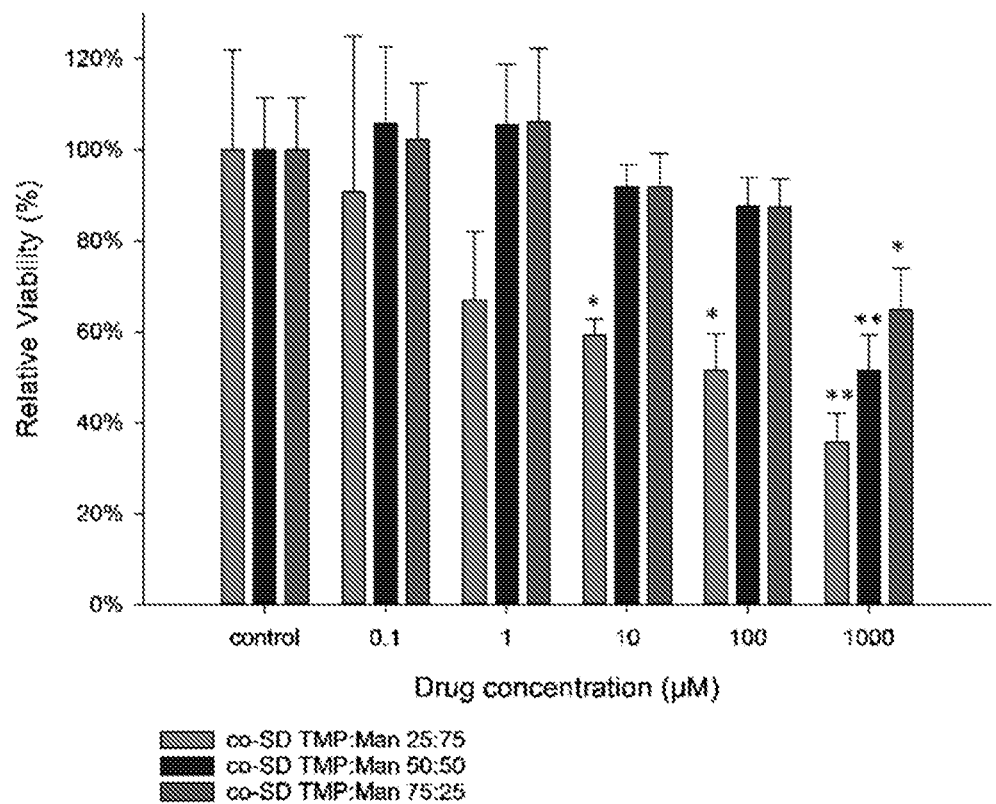

In vitro cell viability was analyzed by exposing H358 and A549 pulmonary cells to different concentrations of representative co-SD TMP: Man powders (at med P). FIG. 21 shows the dose response which indicates that formulated TMP particles are safe for pulmonary drug delivery 72 h after exposure. For A549 there was no significant change in relative viability when they were exposed to TMP in concentrations ranging from 0.1 µM to 100 µM with the exception of co-SD TMP: Man 25:75 which showed relative decrease to 59% at 10 µM and ~51% at 100 µM. There was significant (P<0.05) decrease in cell viability for all the formulations at 1000 µM. After exposing H358 cells to different concentration of the various formulations there was no significant decrease in cell viability at concentrations 1 µM to 100 µM. However, the cells exposed to 1000 µM of the representative formulations showed a significant decrease in cell viability.

In Vitro Transepithelial Electrical Resistance Analysis

Figure 22:
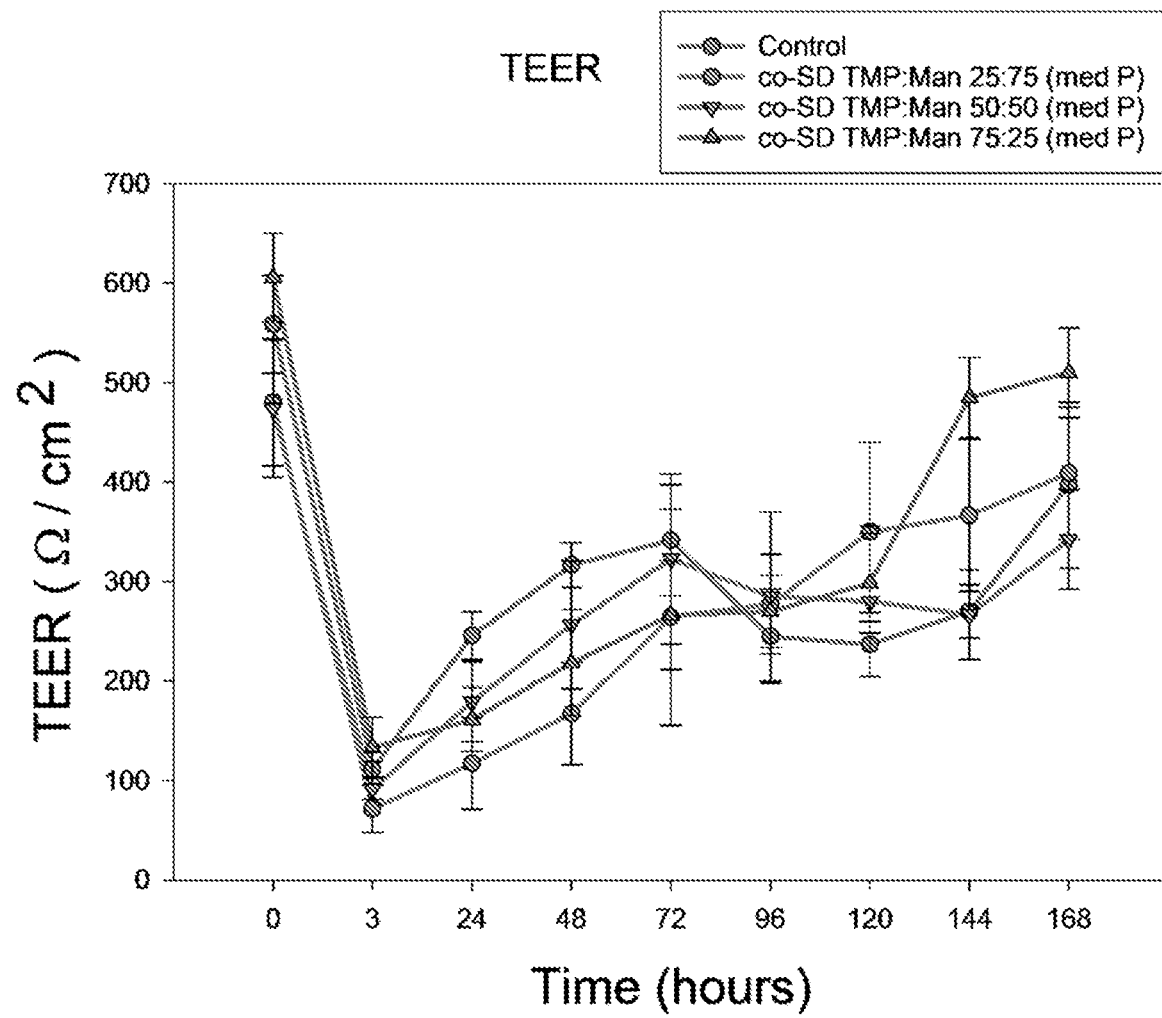
FIG. 22: Transepithelial electrical resistance (TEER) analysis of Calu-3 lung epithelial cells exposed to representative Co-SD particles in air-interface culture (AIC) conditions at 37° C. (n=3, mean SD). Control/no treatment, co-SD TMP: Man 25:75 (med P), co-SD TMP: Man 50:50 (med P), co-SD TMP: Man 75:25 (med P).

Calu-3 cells were exposed to 100 µM of representative co-SD formulations of TMP and Man (med P) in order to determine the effect of these powders on the epithelial cells. A TEER value of at least 500 Ω/cm$^2$ and the visualization via light microscopy of the surface of the transwell inserts confirmed the presence of a complete monolayer of the epithelial cells. After 3 hours of exposure, as it can be seen in FIG. 22 there was a significant decrease in the TEER values, indicating a partial disruption of the monolayer. However, after continuous culturing of the cells it can be seen that in all the formulations there was an increase in the TEER values. Finally, after seven days of culturing, it can be considered that there was a complete recovery of the monolayer. After running a statistical t-test, it can be concluded that there is not a statistically significant difference between the TEER values before the drug exposure and after seven days of cell culturing on each of the formulations (p values>0.05).

This is the first time to report a comprehensive study that illustrates rationally designed co-spray dried tetramethylpyrazine-loaded Mannitol particles via organic solution advanced closed mode spray drying. With this technique, it was possible to produce solid state particles within the narrow size distribution and surface properties desirable for pulmonary inhalation. Furthermore, these particles were specially designed to target the smaller airways and peripheral lung regions. Targeted aerosols lead to lower therapeutic dose and reduced adverse side effects; consequently, they improve the therapeutic outcome. A more exhaustive description of these inhalable particulate systems follows.

The systematic experimental design resulted in solid aerosol formulations of co-SD drug with D-Mannitol as excipient. All designed particles with corresponding spray drying condition are listed in Table 4. Notably, this study revealed that the presence of Man in spray drying solution has enabled TMP molecules to be encapsulated into small spherical particles at different pump rates. Additionally, a significant increase on particle yield (data not shown) during production was observed with the addition of Man. This can be accredited to the hydrogen bonding between TMP and Man, since Man is a hydrogen bond donor/acceptor and TMP is a hydrogen bond acceptor. Similar behavior was also observed on previously designed dimethyl fumarate loaded Man particles using similar spray drying conditions (Muralidharan et al., 2016, supra).

SEM micrographs have shown that majority of co-SD TMP: Man particles were in the nanoparticle/microparticle size range of 0.8-1.5 µm (Tale 5). This is desirable for targeted delivery to the deeper regions of the lung since small diameter particles are characterized to deposit in these regions due to gravitational particle transport mechanisms such as sedimentation and Brownian diffusion (Heyder J. Proceedings of the American Thoracic Society. 2004; 1(4): 315-320). SEM Micrographs also show that majority of the co-SD particles possesses spherical and practically smooth surface compared to raw and SD TMP particles (image not shown). This can be attributed to the presence of Man which has shown improve the surface properties on co-spray drying (Li X, et al., Journal of aerosol medicine and pulmonary drug delivery. 2014; 27(2):81-93). This is advantageous since, during aerosolization of dry powder, particles should possess less interparticulate interactions (i.e., van der Waals forces, capillary forces, electrostatic forces, and mechanical interlocking) which can be reduced by particles with these characteristics (Li X, et al., Journal of pharmaceutical sciences. 2014; 103(9):2937-2949).

XRPD, Raman, and DSC data showed that SD and co-SD particles retained its crystallinity even after spray drying. This was further verified by the birefringence observed during HSM analysis and low residual water content. Crystalline particles with low water content can lead to better physical and chemical stability of the powder for an extended period of time compared to amorphous particles (Thakkar S, et al., Current pharmaceutical design. 2015; 21(40):5789-5801). XRPD sharp and intense peaks are characteristic of long-range molecular order and these can be observed for all the powders. For all co-SD powders, an intense peak at 2θ value of 9.7 is present in the XRPD, representing the presence of Man in delta form (Li et al., 2014, supra).

DSC and HSM analysis demonstrate the stability of the powders at room temperature (25° C.) and body temperature (37° C.) due to lack of phase transitions at these temperatures. The only observable phase transition from solid to liquid state was observed in HSM at the highest temperature of 165° C. for co-SD TMP: Man. However, particles are not expected to be exposed to such temperatures. There was only a single phase transition observed in DSC analysis of co-SD particles, indicating molecular miscibility of the drug with the excipient. Although the presence of TMP molecules could not be established by DSC analysis, its presence was successfully verified in HPLC quantification, resulting in drug loading as high as 0.14 mg per milligram of particles. In addition to the XRPD data, the presence of Man is further verified by ATR-FTIR spectra showing O—H bonding at 3260-3280 cm-1 range which is particularly expressed for Man molecules.

Figure 23A:
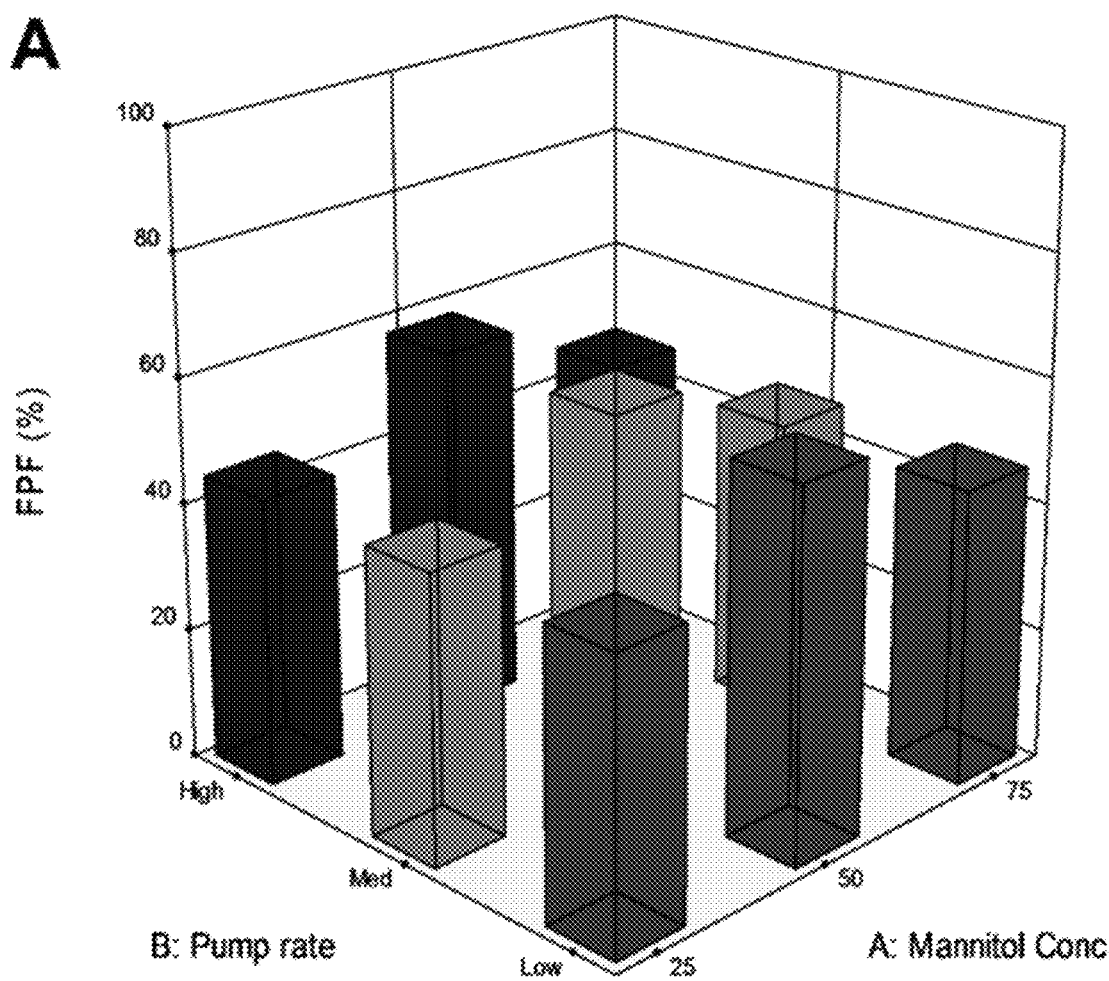
FIG. 23: 3-D surface response plots showing the effect of spray drying pump rate (a pharmaceutical processing property) and chemical composition (a molecular property) on in vitro aerosol dispersion performance of TMP A) Fine Particle Fraction (FPF); B) Emitted Dose (ED); C) Mass Median Aerodynamic Diameter (MMAD).
Figure 23B:
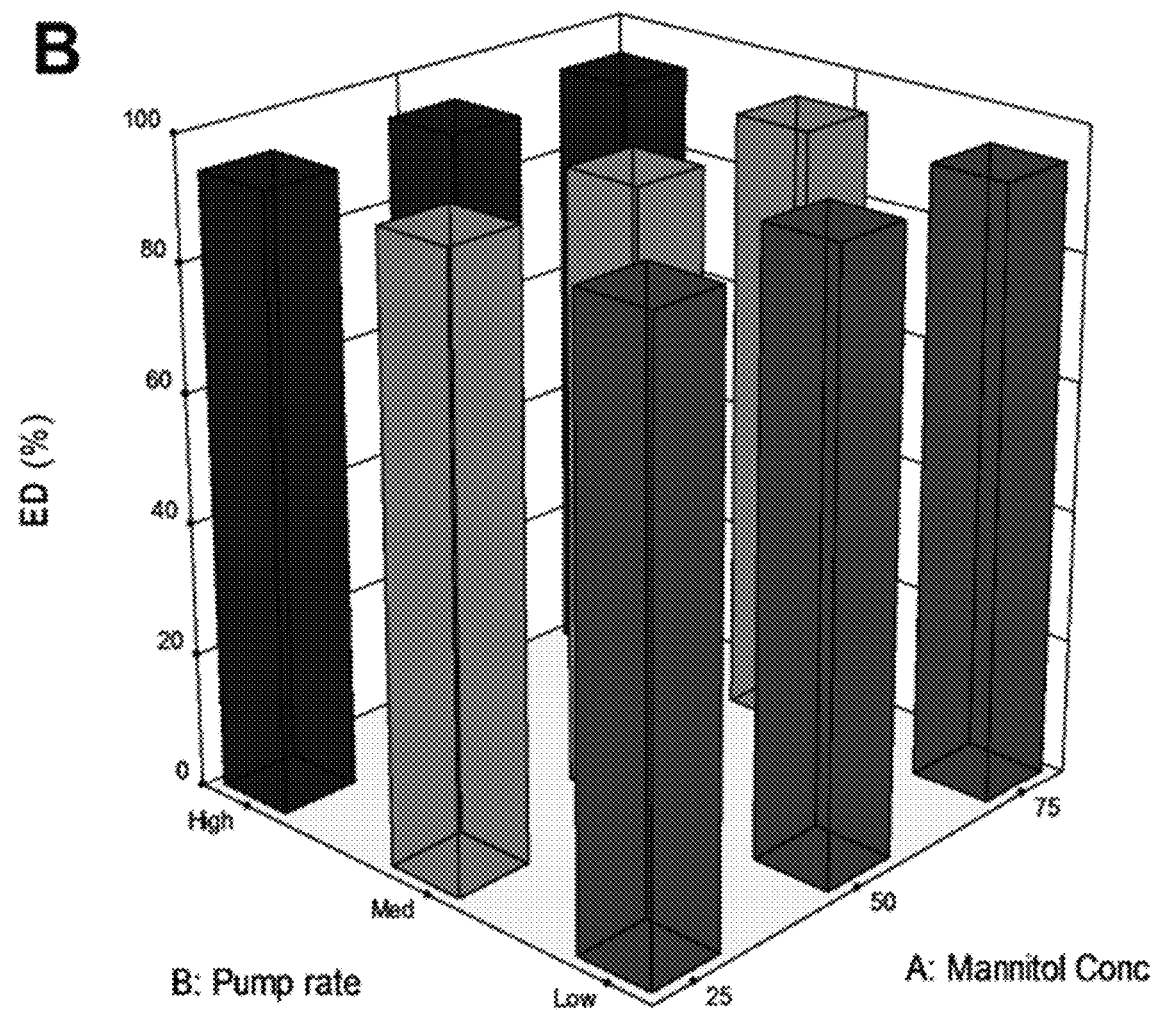
Figure 23C:
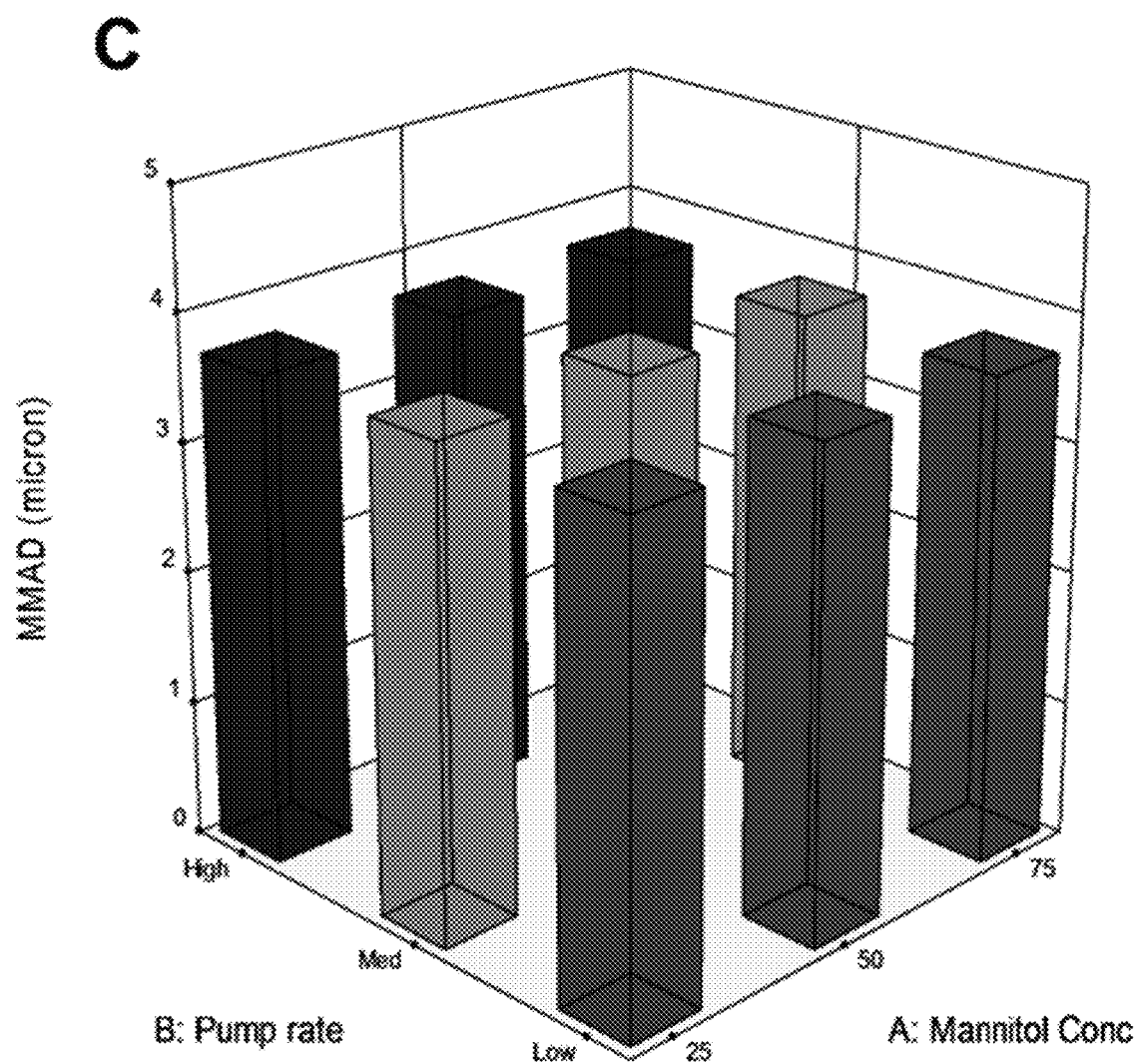

Aerosol dispersion performance was performed at Q of 60 L min$^{-1}$ (adult airflow rate) using a Handihaler® (a high shear stress DPI device). FIG. 23 is a 3-D plot of the aerosol performance of the co-SD TMP: Man powders. Although there is no significant change in ED values with the addition of Man, it is clearly seen from Table 9 and FIG. 23 that it increases FPF and RF for co-SD systems, independently of the pump rate used during spray drying. Furthermore, it is clear that Man helps on the production of smaller particles with resulted MMAD values lower than 5 μm which is indispensable for targeted delivery to the deeper regions of the lung (Oldham M J. Aerosol Science & Technology. 2000; 32(1):61-71). This is in a good agreement with what is seen on SEM micrographs. Change in SD pump rate and Man concentration had little to no effect on the MMAD values. The in vitro aerosol stage deposition shows that most of the single component SD TMP particles deposited on the first stage (above 90%), which would be predicted to deposit in the larger airways in vivo (Marple V A, et al., Part I: Design. *Journal of aerosol medicine.* 2003; 16(3):283-299). On the other hand, co-SD TMP: Man particles achieved deposition from stage 2 to stage 7, which predicts deposition in the smaller airways or even the bronchoalveolar region (Marple et al., supra). Part of this can also be accredited to the low residual water content present in these particles, reducing capillary forces that eventually would lead to a better aerosol dispersion performance (Muralidharan et al, 2016, supra). In addition, small hydrophobic drugs like TMP would be predictable to increase retention of the drug inside the lungs due to favorable interactions with lung cellular membranes (Patton J S, Byron P R. Nature Reviews Drug Discovery. 2007; 6(1):67-74). Hydrophobic drugs are also expected to have lower drug translocation out of the lung, therefore decreasing systemic side effects (Patton and Byron, supra).

In vitro pulmonary cellular viability analysis showed very important findings of co-SD TMP powders cytotoxic activity. The dose response indicates that all formulated powders are safe for pulmonary therapy 72 hours after exposure. The statistical analysis of TEER values (p value>0.05) indicates that Calu-3 epithelial cells are capable of recovering after 7 days of exposure to the drug particles, indicating the safety of these formulations in pulmonary epithelial cells.

This comprehensive and systemic study reports for the first time the design and development of inhalable dry particles consisting of co-spray dried two-component TMP: Man for the treatment of pulmonary arterial hypertension. These were successfully designed for targeted pulmonary delivery using organic solution advanced spray drying in closed-mode. Findings demonstrate the use of Man for the enhancement of particle formation and aerosol performance. These engineered DPI crystalline molecular mixture formulations demonstrate the influence of Man in particle formation during spray drying and the potential of Man to improve aerosol performance through favorable molecular interactions with TMP and retention of crystallinity as molecular mixtures with TMP for the first time. As the results show, these microparticles and nanoparticles showed excellent in vitro aerosol dispersion performance using an FDA-approved human DPI device, predictive modeling their capability of reaching the lower airways. Furthermore, the in vitro pulmonary cellular studies confirmed that these particles can be delivered through the pulmonary route at high concentrations without causing cytotoxicity.

TABLE 5

Particle sizing using image analysis on scanning electron microscopy (SEM) micrographs (N > 100 Particles).

| Powder composition (molar ratio) | Pump rate | Mean size (μm) | Range (μm) | $D_{n10}$ (μm) | $D_{n50}$ (μm) | $D_{n90}$ (μm) | Span (μm) |
|---|---|---|---|---|---|---|---|
| Co-SD TMP: Man 75:25 | High (100%) | 1.146 ± 0.552 | 0.414-3.416 | 0.629 | 0.983 | 1.953 | 1.346 |
| Co-SD TMP: Man 75:25 | Me-high (75%) | 1.456 ± 0.621 | 0.552-4.071 | 0.929 | 1.264 | 2.308 | 1.092 |
| Co-SD TMP: Man 75:25 | Med (50%) | 1.024 ± 0.332 | 0.411-2.064 | 0.633 | 0.949 | 1.459 | 0.870 |
| Co-SD TMP: Man 50:50 | High (100%) | 1.016 ± 0.369 | 0.377-2.590 | 0.642 | 0.953 | 1.528 | 0.930 |
| Co-SD TMP: Man 50:50 | Med-high (75%) | 1.308 ± 0.627 | 0.487-3.469 | 0.665 | 1.141 | 2.296 | 1.430 |
| Co-SD TMP: Man 50:50 | Med (50%) | 1.170 ± 0.585 | 0.388-3.587 | 0.608 | 1.010 | 1.822 | 1.671 |
| Co-SD TMP: Man 25:75 | High (100%) | 1.269 ± 0.445 | 0.496-3.015 | 0.831 | 1.172 | 1.856 | 0.874 |
| Co-SD TMP: Man 25:75 | Med-high (75%) | 1.166 ± 0.338 | 0.092-1.985 | 0.807 | 1.107 | 1.611 | 0.726 |
| Co-SD TMP: Man 25:75 | Med (50%) | 0.812 ± 0.318 | 0.065-2.829 | 0.534 | 0.741 | 1.143 | 0.773 |

TABLE 6

Differential scanning calorimetry (DSC) thermal analysis (n = 3, mean ± SD).

| Powder composition (molar ratio) | Spray drying pump rate (%) | $T_{onset}$ (° C.) | $T_{peak}$ (° C.) | ΔH (J g$^{-1}$) |
|---|---|---|---|---|
| Raw TMP | N/A | 84.53 ± 0.33 | 85.60 ± 0.16 | 152.8 ± 5.7 |
| SD TMP | N/A | 83.41 ± 0.19 | 84.85 ± 0.15 | 179.6 ± 3.6 |
| Co-SD TMP:Man 75:25 | High (100%) | 163.96 ± 0.11 | 165.20 ± 0.04 | 238.6 ± 33.7 |
| Co-SD TMP:Man 75:25 | Med-high (75%) | 162.28 ± 0.82 | 164.20 ± 0.34 | 177.0 ± 44.2 |
| Co-SD TMP:Man 75:25 | Med (50%) | 164.23 ± 0.96 | 165.43 ± 0.66 | 236.1 ± 40.4 |
| Co-SD TMP:Man 50:50 | High (100%) | 163.38 ± 0.27 | 165.08 ± 0.19 | 226.3 ± 12.3 |
| Co-SD TMP:Man 50:50 | Med-high (75%) | 163.77 ± 0.09 | 164.90 ± 0.41 | 226.0 ± 54.4 |
| Co-SD TMP:Man 50:50 | med (50%) | 164.05 ± 0.20 | 165.59 ± 0.17 | 237.8 ± 66.0 |
| Co-SD TMP:Man 25:75 | High (100%) | 163.73 ± 0.28 | 165.33 ± 0.17 | 214.7 ± 32.5 |
| Co-SD TMP:Man 25:75 | Med-high (75%) | 163.62 ± 0.28 | 165.44 ± 0.48 | 214.8 ± 18.7 |
| Co-SD TMP:Man 25:75 | Med (50%) | 163.74 ± 0.27 | 165.08 ± 0.09 | 225.7 ± 37.1 |

TABLE 7

Residual water content for co-SD TMP powders.
(n = 3, ave ± SD).

| Powder composition (molar ratio) | Spray drying pump rate (%) | Residual water content (% w/w) |
|---|---|---|
| Co-SD TMP:Man 75:25 | High (100%) | 1.236 ± 0.519 |
| Co-SD TMP:Man 75:25 | Med-high (75%) | 1.357 ± 0.174 |
| Co-SD TMP:Man 75:25 | Med (50%) | 1.169 ± 0.176 |
| Co-SD TMP:Man 50:50 | High (100%) | 1.384 ± 0.414 |
| Co-SD TMP:Man 50:50 | Med-high (75%) | 1.758 ± 0.358 |
| Co-SD TMP:Man 50:50 | Med (50%) | 0.872 ± 0.039 |
| Co-SD TMP:Man 27:75 | High (100%) | 0.844 ± 0.056 |
| Co-SD TMP:Man 27:75 | Med-high (75%) | 0.864 ± 0.058 |
| Co-SD TMP:Man 27:75 | Med (50%) | 1.096 ± 0.218 |

TABLE 8

Quantification of TMP content in co-SD formulations
(n = 3, ave ± SD).

| Co-SD System (molar ratio) | Pump rate | TMP loading (mg/mg) |
|---|---|---|
| TMP:Man 75:25 | High (100%) | 0.0491 ± 0.0065 |
| TMP:Man 75:25 | Med-high (75%) | 0.1419 ± 0.0196 |
| TMP:Man 75:25 | Med (50%) | 0.0051 ± 0.0004 |
| TMP:Man 50:50 | High (100%) | 0.0014 ± 0.0005 |
| TMP:Man 50:50 | Med-high (75%) | 0.0126 ± 0.0013 |
| TMP:Man 50:50 | Med (50%) | 0.0014 ± 0.0008 |
| TMP:Man 25:75 | High (100%) | 0.0016 ± 0.0002 |
| TMP:Man 25:75 | Med-high (75%) | 0.0045 ± 0.0002 |
| TMP:Man 25:75 | Med (50%) | 0.0028 ± 0.0003 |

TABLE 9

In vitro aerosol dispersion performance using the Next Generation Impactor ® for SD and co-SD aerosol systems including mass median aerodynamic diameter (MMAD), geometric standard deviation (GSD), fine particle fraction (FPF), respirable fraction (RF), and emitted dose (ED)

| SD system | MMAD (μm) | GSD (μm) | FPF (%) | RF (%) | ED (%) |
|---|---|---|---|---|---|
| Co-SD TMP:Man 75:25 (high P) | 3.8 ± 0.3 | 1.9 ± 0.1 | 48.4 ± 1.2 | 78.7 ± 3.4 | 89.6 ± 1.8 |
| Co-SD TMP:Man 75:25 (med-high P) | 4.4 ± 0.5 | 2.0 ± 0.1 | 39.2 ± 2.5 | 69.5 ± 3.7 | 93.1 ± 4.6 |
| Co-SD TMP:Man 75:25 (med P) | 4.1 ± 1.2 | 1.9 ± 0.2 | 50.5 ± 3.4 | 78.4 ± 12.9 | 98.7 ± 0.9 |
| Co-SD TMP:Man 50:50 (high P) | 3.8 ± 0.8 | 1.9 ± 0.2 | 66.8 ± 16.1 | 84.3 ± 4.4 | 94.3 ± 4.5 |
| Co-SD TMP:Man 50:50 (med-high P) | 3.1 ± 0.6 | 1.9 ± 0.1 | 60.0 ± 4.1 | 84.3 ± 7.9 | 98.4 ± 0.5 |
| Co-SD TMP:Man 50:50 (med P) | 4.1 ± 0.5 | 2.1 ± 0.2 | 51.0 ± 3.1 | 76.9 ± 97.4 | 97.4 ± 4.0 |
| Co-SD TMP:Man 25:75 (high P) | 3.4 ± 0.3 | 1.9 ± 0.1 | 50.0 ± 6.6 | 80.1 ± 9.0 | 96.8 ± 3.8 |
| Co-SD TMP:Man 25:75 (med-high P) | 3.5 ± 0.2 | 1.8 ± 0.1 | 47.4 ± 1.4 | 84.2 ± 2.6 | 97.9 ± 1.0 |
| Co-SD TMP:Man 25:75 (med P) | 3.6 ± 0.4 | 1.9 ± 0.1 | 44.8 ± 4.0 | 80.3 ± 4.5 | 94.5 ± 3.8 |

All publications and patents mentioned in the present application are herein incorporated by reference. Various modification and variation of the described methods and compositions of the disclosure will be apparent to those skilled in the art without departing from the scope and spirit of the disclosure. Although the disclosure has been described in connection with specific preferred embodiments, it should be understood that the disclosure as claimed should not be unduly limited to such specific embodiments. Indeed, various modifications of the described modes for carrying out the disclosure that are obvious to those skilled in the relevant fields are intended to be within the scope of the following claims.

We claim:

1. A composition comprising crystalline particles of tetramethylpyrazine (TMP) with X-Ray Powder Diffraction (XRPD) peaks at 16.56°, 19.00°, 24.83°, and 27.56°, wherein said TMP particles are generated by a method, comprising: a) preparing a first solution comprising said TMP in methanol; and b) spraying said first solution using a spray drying apparatus.

2. The composition of claim 1, wherein said first solution further comprises a pharmaceutically acceptable carrier.

3. The composition of claim 1, wherein said pharmaceutically acceptable carrier is D-mannitol.

4. The composition of claim 3, wherein said TMP and D-mannitol are present at a molar ratio of 75:25 to 25:75 TMP:D-mannitol.

5. The composition of claim 1, wherein said TMP particles have a diameter of 0.8-1.5 μm.

6. The composition of claim 1, wherein said method further comprises the steps of preparing a second solution comprising said pharmaceutically acceptable carrier in methanol; and co-spraying said first and second solutions.

7. A system, comprising:
a) the composition of claim 1; and
b) a dry powder inhaler device.

8. A method of treating pulmonary arterial hypertension (PAH) in a subject, comprising:
administering the composition of claim 1 to a subject diagnosed with or having signs or symptoms of PAH under conditions such that said signs or symptoms are reduced.

9. The method of claim 8, wherein said signs or symptoms of PAH include a pulmonary arterial pressure of greater than or equal to 22 mmHg at rest of 30 mmHg during exercise.

10. The method of claim 8, further comprising administering an additional treatment for PAH.

11. The method of claim 10, wherein said additional treatment is selected from the group consisting of a vasodilator, an anticoagulant, an antiplatelet agent, an anti-inflammatory agent, and a vascular-remodeling therapy.

12. The method of claim 8, wherein said composition is administered to the lung of said subject using the system of claim 7.

* * * * *